US007723289B2

(12) United States Patent
Barnea

(10) Patent No.: US 7,723,289 B2
(45) Date of Patent: *May 25, 2010

(54) PIF TETRAPEPTIDES

(75) Inventor: Eytan R. Barnea, Cherry Hill, NJ (US)

(73) Assignee: BioIncept, LLC, Cherry Hill, NJ (US)

( * ) Notice: Subject to any disclaimer, the term of this patent is extended or adjusted under 35 U.S.C. 154(b) by 960 days.

This patent is subject to a terminal disclaimer.

(21) Appl. No.: 11/110,990

(22) Filed: Apr. 20, 2005

(65) Prior Publication Data

US 2008/0003178 A1   Jan. 3, 2008

Related U.S. Application Data

(63) Continuation-in-part of application No. 10/971,760, filed on Oct. 22, 2004.

(60) Provisional application No. 60/513,370, filed on Oct. 22, 2003.

(51) Int. Cl.
*A61K 38/00* (2006.01)

(52) U.S. Cl. .................... 514/2; 424/184.1; 424/278.1; 530/330

(58) Field of Classification Search ........................ None
See application file for complete search history.

(56) References Cited

U.S. PATENT DOCUMENTS

| | | | | |
|---|---|---|---|---|
| 5,279,941 | A | * | 1/1994 | Lessey ...................... 435/7.21 |
| 5,646,003 | A | | 7/1997 | Barnea et al. |
| 5,981,198 | A | | 11/1999 | Barnea et al. |
| 6,585,979 | B1 | | 7/2003 | Berman |
| 2003/0099643 | A1 | | 5/2003 | June et al. |
| 2005/0064520 | A1 | | 3/2005 | Barnea et al. |
| 2008/0269137 | A1 | | 10/2008 | Barnea |
| 2009/0081225 | A1 | | 3/2009 | Barnea |

FOREIGN PATENT DOCUMENTS

| | | | |
|---|---|---|---|
| WO | WO 9526982 | A2 * | 10/1995 |
| WO | WO 02053092 | A2 * | 7/2002 |
| WO | WO 03/004601 | A | 1/2003 |
| WO | WO 2004/053086 | A | 6/2004 |
| WO | WO 2005/040196 | A2 | 5/2005 |

OTHER PUBLICATIONS

Rose et al., Manual of Clinical Laboratory Immunology, 5th edition, 1997, ASM Press, pp. 20-48.*
Janeway et al., Immunobiology, 3rd edition. 1997, Garland Publishing Inc., pp. 7:25 and 9:31.*
Goodnow CC., Lancet. Jun. 30, 2001;357(9274):2115-21.*
Skyler, J.S., et al. Diabetes Care. 2005;28:1068-1076.*
Pozzilli, P., et al. Diabetol. 2000;43:1000-1004.*
Dong, V.M., et al. Ped. Transplant . . . 1999;161:181-189.*
Bell, J.J. et al. J. Immunol. 2008;180:1508-1516.*
Kraus, T.A., and Mayer, L. Curr. Opin. Gastroenterol. 2005;21:692-696.*
Schroeder, R.A., et al. J. Surg. Sci. Res. 2003;111:109-119.*
Chaouat, J. Reprod. Fert. 1990, 89:447-458.*
Tangri et al., J. Immunol., 1994, 152:4903-4911.*

Marketletter, Sep. 13, 1999, 2 pages.*
Barnea, *Embryo-Maternal Dialogue: Linking Pregnancy Recognition and Proliferation Control*, Rochester Trophoblast Conference 2000, under the auspices of the Trophoblast Conference and SIEP, the Society for the Investigation of Early Pregnancy, Rochester, NY.
Ripka et al., Peptidomimetic design, 1998, Curr. Op. Chem. Biol. 2:441-452.
Hrbuy et al., Synthesis of oligopeptide and peptidomimetic libraries, 1997, Curr. Op. Chem. Biol. 1:114-119.
Hruby et al., Conformational and topographical considerations in designing agonist peptidomimetics from peptide leads, 2000, Curr. Med. Chem. Sept.. 7(9): 945-970.
Barnea et al., *Progress in characterization of pre-implantation factor in embryo cultures and in vivo*, 1999, Am. J. Reprod. Immunol. 00.
Barnea, *The Embryo: a privileged entity in a privileged site: lessons learnt from embryonal development*, 1997, Early Pregnancy: Biol. & Med., 3:77-80.
Barnea, *Current Progress in Early Pregnancy Investigation and the Steps Ahead Part I*, 2000, Early Pregnancy Biology & Medicine, 4:1-4 (SIEP Publ @ www.earlypregnancy.org).
Barnea et al., *Embryo-maternal signaling prior to implantation*, 2001, in Obstetrics & Gynecology, Section 2 Human Reproduction—Anatomy, Physiology, Embryology, Munteanu Ed. (Romanian Academy of Science Publishers), pp. 112-117.
Roussev et al., *Embryonic origin of preimplantation factor (PIF): biological activity and partial characterization*, 1996, Mol. Human Reprod., 2, No. 11:883-887.
Barnea, *EnVision the field of Early Pregnancy Investigation*, 1995, Early Pregnancy: Biol. & Med., 1:169-170.
Rayburn, *Embryonic Medicine and Therapy*, 1999, (Jauniaux, E., Barnea, E.R., Edwards, R.G., eds.) The New England Journal of Medicine Book Review, 340(19):1519.
Barnea, Keynote Editorial: *New Frontiers in Early Pregnancy Investigation*, 1995, Early Pregnancy: Biol. & Med. 1:1-3.
Barnea et al., Editorial: *Reflections on early pregnancy: organizing chaos or organized chaos?*, 1996, Early Pregnancy: Biol. & Med. 2:77-79.
Barnea et al., *Use of Lymphocyte Platelet Binding Assay for Detecting a Preimplantation Factor: A Quantitative Assay*, 1994, Am. J. Reprod. Immunol. 32:133-138.
Boklage, Survival probability of human conceptions from fertilization to term, Int J Fertil Mar.-Apr. 1990, 35(2): 75, 79-80, 81-94.
Barnea et al., *Immune System (IS) and Proliferation Control (PC) from Embryo to Adulthood: Roles of Preimplantation Factor (PIF) and Developmental Proteins (DPs)*, 2001, Renaissance Congress of the 21st Century: The Woman and Child Before, During and After Pregnancy, A Global union of Scientific Congresses, under the high patronage of the President of the Italian Republic, 5th SIEP World Conference, 1st International Congress of the Mediterranean Society of Reproduction and Neonatology, 4th International Congress of the International Society for New Technology in Gynecology, Reproduction and Neonatology, Rome, Italy.

(Continued)

Primary Examiner—Michael Szperka
(74) Attorney, Agent, or Firm—Pepper Hamilton LLP

(57) ABSTRACT

Peptides and peptidomimetics capable of enhance endometrial receptivity, blocking activated but not basal immunity, inhibiting cell proliferation and creating a $T_H2$ type cytokine bias are disclosed. The peptides and mimetics are based upon the C-terminal tetrapeptide of PIF peptides. Also disclosed are methods of using these peptides and peptidomimetics for therapeutic and diagnostic purposes.

6 Claims, 23 Drawing Sheets
(20 of 23 Drawing Sheet(s) Filed in Color)

OTHER PUBLICATIONS

Coulam et al., *Preimplantation Factor (PIF) Predicts Subsequent Pregnancy Loss*, 1995, Am. J. Reprod. Immunol. 34:88-92.

Barnea et al., *Embryonic Signals*, in Jauniaux, 1997, Jauniaux, E., Barnea, E.R., Edwards, R.G. (eds.) Embryonic Medicine and Therapy, pp. 63-75 (Oxford University Press).

Barnea, *Underlying mechanisms and treatment of early pregnancy failure*, 2001, Ferti Magazine, Ferti.Net Worldwide Fertility Network, Apr. 1-4.

Navot et al., *Poor oocyte quality rather than implantation failure as a cause of age-related decline in female fertility*, Lancet Jun. 8, 1991: 337(8754):1375-1377 (abstract).

Mirhashemi, *Cancer and Pregnancy*, 2002, (Barnea, E.R., Jauniaux, E., Schwartz, P.E., eds.) New England J Med Book Review, Jun. 13, 346(24):1921.

Roussev et al., A Novel Bioassay for Detection of Preimplantation Factor (PIF), 1995, Am J Reprod. Immunol. 33:68-73.

Roussev et al., *Development and Validation of an Assay for Measuring Preimplantation Factor (PIF) of Embryonal Origin*, 1996, Am. J. Reprod. Immunol. 35:281-287.

Barnea et al., 2000, *Maternal Immune Response to Trophoblast*, GTD and Cancer, In: Shoenfeld, Y. and Gerhwin, M.E. (eds) Cancer and Autoimmunity, pp. 343-350, Elsevier Science B.V. Publishers.

Barnea et al., *Identification and Validation of an Assay for Preimplantation Factor (PIF)*, 1994, Society for Gynecologic Investigation 41$^{st}$ Meeting, April, Chicago, IL (abstract).

Roussev et al., *Clinical Validation of Preimplantation Factor (PIF) Assay*, 1994, Second World Conference on Implantation and Early Pregnancy in Humans, May, Atlantic City, NJ (abstract).

Roussev et al., 1994, *A Novel Bioassay for Detection of Preimplantation Factor (PIF)*, American Society of Reproductive Immunology, XVI Annual Meeting, June, Philadelphia, PA (abstract).

Coulam et al., *Preimplantation Factor (PIF) Predicts Subsequent Pregnancy Loss*, 1994, The American Fertility Society 50$^{th}$ Annual Meeting, November, San Antonio, TX (abstract).

Roussev et al., *Embryonic Origin of Preimplantation Factor (PIF)*, 1995, Society for Gynecological Investigation 42$^{nd}$ Meeting, Chicago, IL (abstract).

Barnea et al., *Partial Characterization of Embryo-Derived Preimplantation Factor (PIF)*, 2006, Ninth World Congress on Human Reproduction, May, Philadelphia, PA (abstract).

Barnea et al., *Preimplantation Factor (PIF): Current Developments*, 1996, Third World Conference on Early Pregnancy—An Interdisciplinary Approach, October, Atlantic City, NJ (abstract).

Barnea et al., 1998, *Partial Characterization of Mammalian Preimplantation Factor in Culture and In Vivo*, Fourth International Meeting Mechanisms in Local Immunity: and Joint Meeting Fourth Meeting of Alps Adria Society for Immunology of Reproduction (AASIR), September, Opatija, Croatia (abstract).

Barnea, *Preimplantation Factor: A specific embryo viability factor*, 1999, The First National Congress on Human Assisted Reproduction with International Participation under the patronage of the Romanian Academy, Timisoara, Romania (abstract).

Gonzales et al., *Preimplantation factor (PIF) could be a portion of CD2 or a homologue peptide*, 2001, 57$^{th}$ Annual Meeting of the American Society for Reproductive Medicine, Orlando, FL (abstract).

Barnea, *Safeguards established at conception influence peri and postnatal life: Roles of Preimplantation Factor (PIF) and Developmental Proteins (DPs)*, 2001, World Congress of Perinatal Medicine, Parallel Scientific SIEP Meeting, Sep. 23-27, Barcelona, Spain (abstract).

Barnea, *Novel Preimplantation Factors (PIF) and Developmental Peptides (DPs) are involved in safeguarding pregnancy*, 2002, The Fetus as a Patient, Budapest, Hungary (abstract).

Gonzales et al., *Preimplantation factors (PIF) embryo-derived immunomodulatory peptides: possible implications for maternal recognition and allograft tolerance*, 2002, 22$^{nd}$ Annual Meeting of the American Society for Reproductive Immunology, Chicago, IL (abstract).

Gonzalez et al., Immunomodulatory features of preimplantation factors (PIF) from mouse embryos, 2002, 11$^{th}$ World Conference on Human Reproduction, June, Montreal, Canada.

Paidas et al, *Pregnancy Implantation Factor (PIF) Activity is Correlated with a Pro-Inflammatory Response*, 2002, 23$^{rd}$ Annual Society for Maternal-Fetal Medicine Conference, San Francisco, CA (abstract).

Barnea et al., Identification and Validation of an Assay for Preimplantation Factor (PIF), 1994, Second World Conference on Implantation and Early Pregnancy in Humans, May, Atlantic City, NJ (abstract).

Gardner et al., Culture of viable human blastocysts in defined sequential serum-free media, 1998, Human Reprod. June: 13, Suppl 3: 148-159.

Barnea et al., *Preimplantation Signalling by the Embryo*, 3$^{rd}$ World Conference on Early Pregnancy, Oct. 3-6, 1996 (abstract).

Raghupathy, The 1-type immunity is incompatible with successful pregnancy, 1997, Immunol. Today 18: 478 (abstract).

Wegmann et al., Bidirectional cytokine interactions in the maternal-fetal relationship: is successful pregnancy a TH2 phenomenon? 1993, Immunol. Today 14, 353-356 (abstract).

Cavanagh et al, The purification of early-pregnancy factor to homogeneity from human platelets and identification as chaperonin 10, 1994, Eur. J. Biochem. 222: 551-560 (abstract).

Piccinni et al., Production of IL-4 and leukemia inhibitory factor by T cells of the cumulus oophorus: a favorable microenvironment for pre-implantation embryo development, 2001, Eur. J. Immunol., Aug: 31(8), 2431-2437(abstract).

Wickramasinghe et al., Blood and bone marrow changes in malaria, 2000, Baillieres Best. Pract. Res. Clin. Haematol. June:13(2), 277-299 (abstract).

Romagnani, Lymphokine production by human T cells in disease states, 1994, Annu. Rev. Immunol. 12, 227-257 (abstract).

Chaouat et al., IL-10 prevents naturally occurring fetal loss in the CBA x DBA/2 mating combination, and local defect in IL-10 production in this abortion-prone combination is corrected by in vivo injection of IFN-tau, 1995, J. of Immunol. 154, 4261-4268 (abstract).

Ho et al., Distribution of Th1 and Th2 cell populations in human peripher and decidual T cells from normal and anembryonic pregnancies, 2001, Fertil. Steril. Oct:76(4): 797-803 (abstract).

Wu et al., Increase in the production of interleukin-10 early after implantation is related to the success of pregnancy, 2001, Am. J. Reprod. Immunol. Dec:46(6): 386-392 (abstract).

Choudhury et al., Human reproductive failure I: Immunological factors, 2000, Hum. Reprod. Update 7:113-134.

Heyner, Growth factors in preimplantation development: role of insulin and insulin-like growth factors, 1997, Early Preg. Biol and Med 3: 153-163.

Abbas et al., Functional diversity of helper T lymphocytes, 1996, Nature 383: 787-793.

Taubes, Malaria Parasite Outwits the Immune System, 2000, Science 290: 435.

Barnea et al., *Implantation*, 2001, in Obstetrics & Gynecology, Section 2 Human Re production—Anatomy, Physiology, Embryology, Munteanu Ed. (Romanian Academy of Science Publishers), pp. 117-123 (TOC only).

Barnea et al., *Evolution of feto-placental unit*, in Obstetrics & Gynecology, 2001, Section 2 Human Re production—Anatomy, Physiology, Embryology, Munteanu Ed. (Romanian Academy of Science Publishers), pp. 170-175.

Morgan et al., Approaches to the Discovery of Non-Peptide Ligands for Peptide Receptors and Peptidases, 1989, Annual Reports Medicinal Chem.24: 243-252.

Ripka et al., Peptidomimetic design, 1998, Curr Opin in Chem Biol. 2:441-452.

Hruby et al., Synthesis of oligopeptide and peptidomimetic libraries, 1997, Curr Opin in Chem Biol. 1:114-119.

Hruby et al., Conformational and Topographical Considerations in Designing Agonist Peptidomimetics from Peptide Leads, 2000, Current Medicinal Chem. 7:945-970.

Stewart et al., Preimplantation Development of Mammalian Embryo and Its Regulation by Growth Factors, 1997, Dev. Genetics 21:91-101.

Gonzalez et al. "Preimplantation Factor (PIF) May Modulate Maternal Cellular Immunity (CD2)" 1998, SIEP, The Society for the Investigation of Early Pregnancy, BioIncept, Inc., BBRI, Boston Biomedical Research Institute, p. 68-69.

Barnea, Insight into Early Pregnancy Events: The Emerging Role of the Embryo, 2004, Am. J. Reprod. Immunol. 51:319-322.

Gonzalez et al. "Preimplantation Factors (PIF) Embryo-Derived Immunomodulatory Peptides: Possible Implications for Maternal Recognition and Allograft Tolerance" 2002, American Journal of Reproductive Immunology, vol. 47, No. 6, p. 347.

Schumacher et al. Primer on the Rheumatic Diseases, 10$^{th}$ edition, 1993, Arthritis Foundation, pp. 86-89 and 100-105.

Barnea et al. "Applying Embryo-Derived Immune Tolerance to the Treatment of Immune Disorders" 2007, Annals of the New York Academy of Sciences, 1110: 602-618.

\* cited by examiner (A) Fluorescence-labeled sPIF-1 binding to human Lymphocytes.
(B) Binding to the total PMBC population
(C) Binding to lymphocytes that form rosettes with platelets, P-L bioassay.

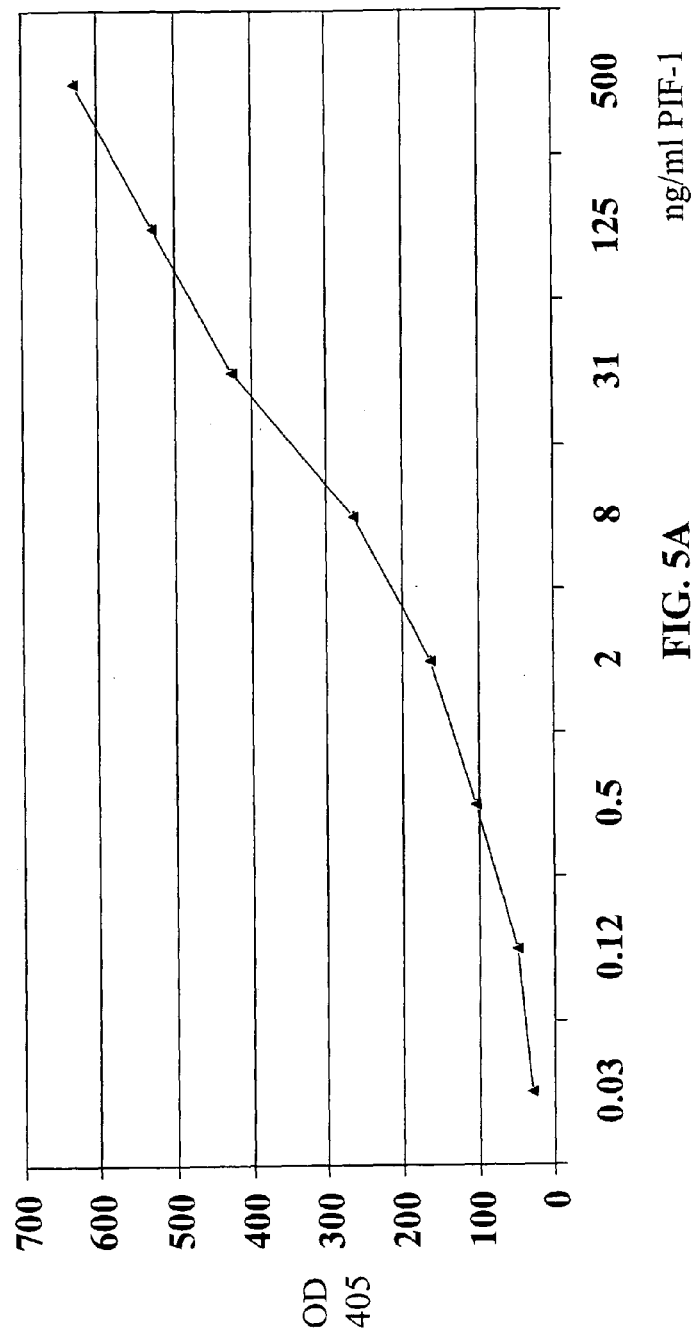

FIG. 5A sPIF-1 ELISA STANDARD CURVE
PIF ANTIBODY DETECTS LOW sPIF LEVELS (pg)

Polyclonal antibodies were generated against PIF-1 in rabbits (COVANCE Inc.). High titers 50% at 1:50,000 were achieved. Serial dilutions of synthetic PIF-1 were plated, blocked and then washed off. PIF-1 antibody (1:5000) was added incubated and washed off. Goat anti-rabbit antibody was added, incubated and washed off. Reaction was stopped by SDS and counted in plate reader (Biosynthesis Inc, G Vandydriff)

PIF-1 EXPRESSION IN HUMAN PLACENTA
Differences with Western Blot

FIRST TRIMESTER: MAb, IgY, IgG
TERM: IgY, IgY, IgG

Tissue extract affinity purified IgG and IgY and MAb were probed 1/200-1/50 dilution followed by II Ab A) HPLC profile of first trimester PPS in a preparative column. B) HPLC profile of PPS-3kDa previous purified by MabCD2 affinity chromatography C) HPLC profile of a PIF + peak from PPS-3kDa previous purified by MabCD2 chromatography affinity and HPLC

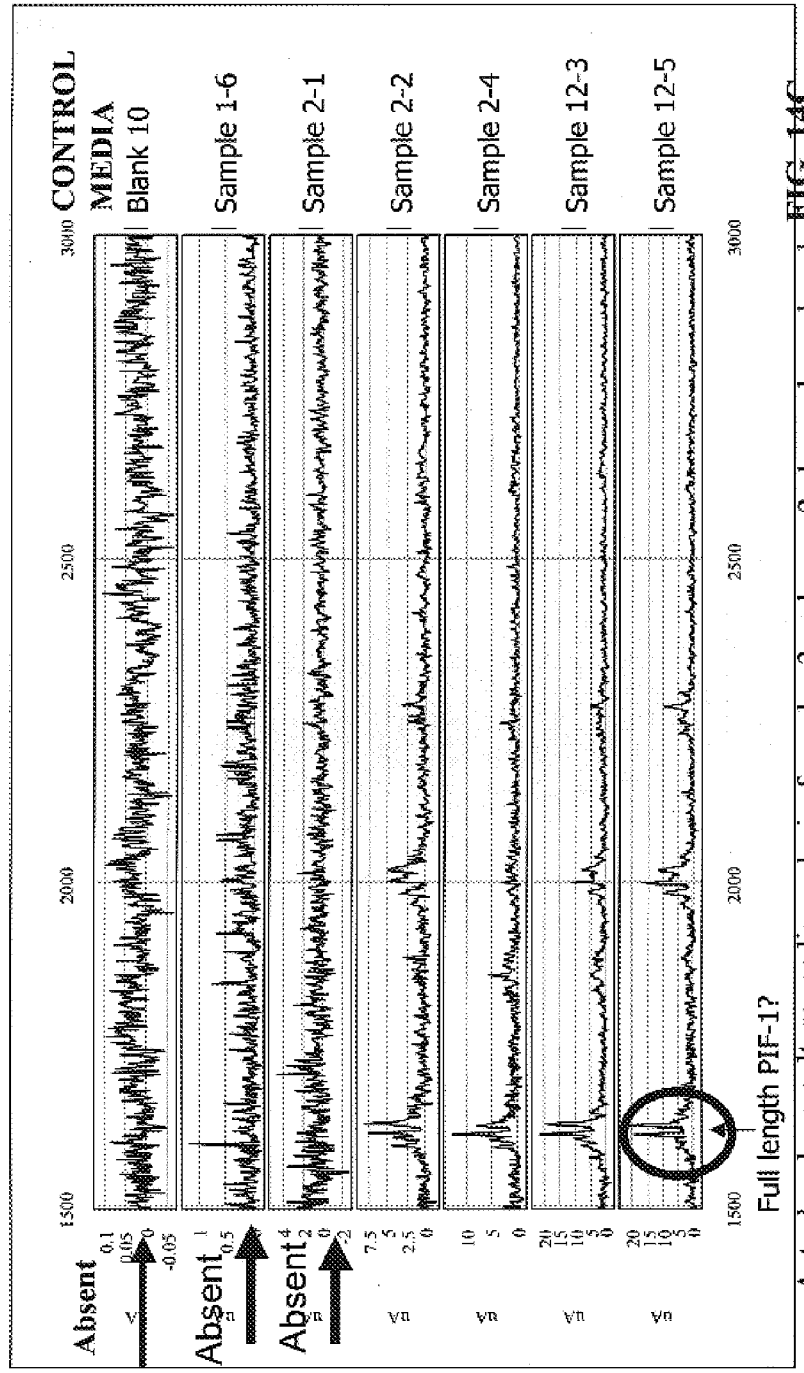

NO PIF IN PLACENTA - PREMATURE DELIVERY
Preterm 26 weeks at 24 hours culture
Preterm 26 weeks at 24 hours culture IFN-g treated
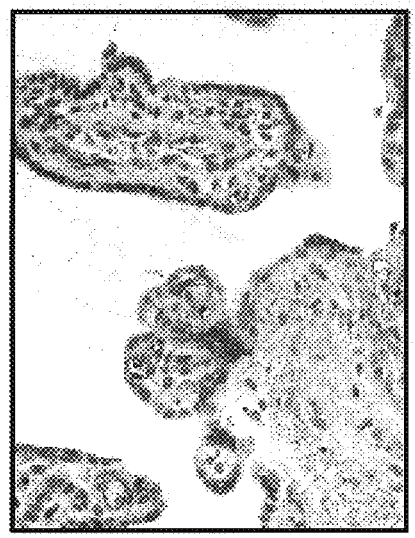
Preterm placenta, 26 weeks at 0 hours
Confirmed in 5 different placenta
FIG. 15

PIF-1 ANTIBODY TESTING OF PREGNANT VS NON PREGNANT SERUM
Differences in HMW Bands in Pregnant Cow Serum Noted Pig−  Pig+  Cow−  Cow+  Horse−  Horse+

Western blot 1/200 affinity purified PIF-1 IgG, followed by Goat anti rabbit IgG HRP

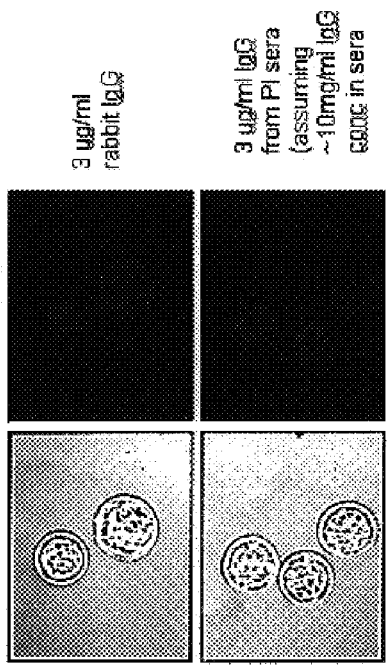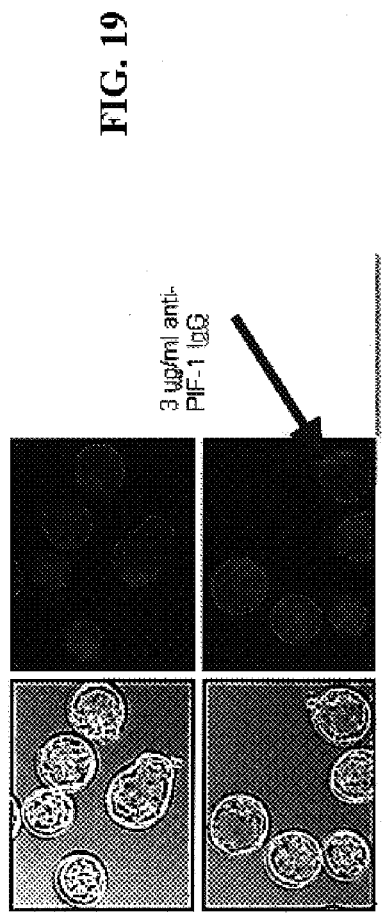
FIG. 19

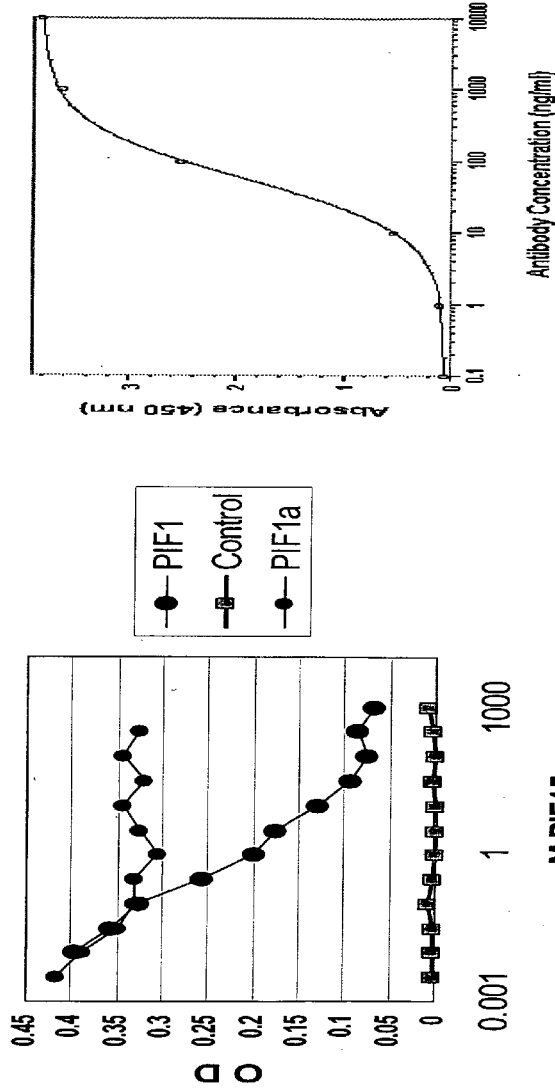

SEQUENCE LISTING

<160> NUMBER OF SEQ ID NOS: 23

<210> SEQ ID NO 1
<211> LENGTH: 15
<212> TYPE: PRT
<213> ORGANISM: Mus musculus

<400> SEQUENCE: 1

Met Val Arg Ile Lys Pro Gly Ser Ala Asn Lys Pro Ser Asp Asp
1               5                   10                  15

<210> SEQ ID NO 2
<211> LENGTH: 15
<212> TYPE: PRT
<213> ORGANISM: Mus musculus

<400> SEQUENCE: 2

Met Val Arg Ile Lys Tyr Gly Ser Tyr Asn Asn Lys Pro Ser Asp
1               5                   10                  15

<210> SEQ ID NO 3
<211> LENGTH: 13
<212> TYPE: PRT
<213> ORGANISM: Mus musculus

<400> SEQUENCE: 3

Met Val Arg Ile Lys Pro Gly Ser Ala Asn Lys Pro Ser
1               5                   10

<210> SEQ ID NO 4
<211> LENGTH: 9
<212> TYPE: PRT
<213> ORGANISM: Mus musculus

<400> SEQUENCE: 4

Met Val Arg Ile Lys Pro Gly Ser Ala
1               5

<210> SEQ ID NO 5
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 5

Gly Arg Val Asp Pro Ser Asn Lys Ser Met Pro Lys Asp Ile Ala
1               5                   10                  15

<210> SEQ ID NO 6
<211> LENGTH: 10
<212> TYPE: PRT
<213> ORGANISM: Mus musculus

<400> SEQUENCE: 6

Ser Gln Ala Val Gln Glu His Ala Ser Thr
1               5                   10

<210> SEQ ID NO 7
<211> LENGTH: 13
<212> TYPE: PRT
<213> ORGANISM: Mus musculus

<400> SEQUENCE: 7

-continued

Ser Gln Ala Val Gln Glu His Ala Ser Thr Asn Met Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: SYNTHETIC PEPTIDE

<400> SEQUENCE: 8

Glu Val Ala Gln His Ser Gln Ala Ser Thr Met Asn Gly
1               5                   10

<210> SEQ ID NO 9
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 9

Gly Gln Ala Ser Ser Ala Gln Met Asn Ser Thr Gly Val His
1               5                   10

<210> SEQ ID NO 10
<211> LENGTH: 18
<212> TYPE: PRT
<213> ORGANISM: Mus musculus

<400> SEQUENCE: 10

Ser Gly Ile Val Ile Tyr Gln Tyr Met Asp Asp Arg Tyr Val Gly Ser
1               5                   10                  15

Asp Leu

<210> SEQ ID NO 11
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 11

Gly Met Arg Glu Leu Gln Arg Ser Ala Asn Lys
1               5                   10

<210> SEQ ID NO 12
<211> LENGTH: 9
<212> TYPE: PRT
<213> ORGANISM: Mus musculus

<400> SEQUENCE: 12

Val Ile Ile Ile Ala Gln Tyr Met Asp
1               5

<210> SEQ ID NO 13
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 13

Met Val Arg Ile Lys Pro Gly Ser Ala Asn Lys Pro Ser Asp Asp
1               5                   10                  15

```
<210> SEQ ID NO 14
<211> LENGTH: 13
<212> TYPE: PRT
<213> ORGANISM: Artificial Sequence
<220> FEATURE:
<223> OTHER INFORMATION: SYNTHETIC PEPTIDE

<400> SEQUENCE: 14

Ser Gln Ala Val Gln Glu His Ala Ser Thr Asn Met Gly
1               5                   10

<210> SEQ ID NO 15
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 15

Ser Gly Ile Val Ile Tyr Gln Tyr Met Asp Asp Arg Tyr Val Gly Ser
1               5                   10                  15

Asp Leu

<210> SEQ ID NO 16
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 16

Met Val Arg Ile Lys Pro Gly Ser Ala
1               5

<210> SEQ ID NO 17
<211> LENGTH: 9
<212> TYPE: PRT
<213> ORGANISM: Artificial Sequence
<220> FEATURE:
<223> OTHER INFORMATION: SYNTHETIC PEPTIDE

<400> SEQUENCE: 17

Val Ile Ile Ile Ala Gln Tyr Met Asp
1               5

<210> SEQ ID NO 18
<211> LENGTH: 5
<212> TYPE: PRT
<213> ORGANISM: Artificial Sequence
<220> FEATURE:
<223> OTHER INFORMATION: SYNTHETIC PEPTIDE

<400> SEQUENCE: 18

Met Val Arg Ile Lys
1               5

<210> SEQ ID NO 19
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 19

Pro Gly Ser Ala
```

```
<210> SEQ ID NO 20
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 20

Ala Val Arg Ile Lys Pro Gly Ser Ala Asn Lys Pro Ser Asp Asp
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: SYNTHETIC PEPTIDE

<400> SEQUENCE: 21

Val Arg Ile Lys Pro Gly Ser Ala Asn Lys Pro Ser Asp Asp
1               5                   10

<210> SEQ ID NO 22
<211> LENGTH: 15
<212> TYPE: PRT
<213> ORGANISM: Artificial Sequence
<220> FEATURE:
<223> OTHER INFORMATION: SYNTHETIC PEPTIDE

<400> SEQUENCE: 22

Gln Val Arg Ile Lys Pro Gly Ser Ala Asn Lys Pro Ser Asp Asp
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 23

Glu Ala Ile Tyr Ala Ala Pro Phe Ala Lys Lys Lys
1               5                   10
```

PIF TETRAPEPTIDES

CROSS REFERENCES TO RELATED APPLICATIONS

This application is a continuation-in-part of U.S. application Ser. No. 10/971,760 filed Oct. 22, 2004, which claims priority from U.S. Provisional Application No. 60/513,370 filed Oct. 22, 2003 and U.S. Ser. No. 10/482,244 filed Dec. 22, 2003, the contents of which are incorporated herein by reference in their entirety.

BACKGROUND

Fertilization requires the proper interaction between the egg and sperm. Such a targeted event, even under natural conditions, is random, and hence the genetic make up of the nascent genome is unpredictable. The impending pregnancy has to prepare the maternal environment towards acceptance of a semi- or even a total allograft. This preparation can be divided to four distinct phases; the first is the pre-fertilization period, the second is the fertilization/post fertilization, the third phase is trophoblast development, and the final fourth phase is the implantation period.

The first phase, which is the pre-fertilization period, takes place during follicular development. The egg is surrounded by the cumulus oophorus and it is bathed in the rich follicular fluid. This fluid has some immune suppressive activity that may facilitate the fertilization process as well as post-fertilization development. This immune suppressive activity is required, due to the fact that shortly after fertilization, expression of foreign antigens, caused by the sperm, may be present. This mechanism, however, is not a necessary requirement. In cases of in vitro fertilization, no such fluid is available, and fertilization takes place without difficulty in an artificial environment. Moreover, women who have no ovaries can get pregnant by donor embryo transfer.

The next phase is the fertilization/post fertilization process. Once the sperm penetrates the egg it becomes "non visible" by the maternal environment. During the process of egg and sperm head fusion, as long as the egg surface membrane does not change its characteristics and become recognizable by the maternal immune system, no immune reaction would be expected. To safeguard the fertilized egg, it is rapidly surrounded by the zona pellucida, which is a hard and impenetrable shell designed to ward off immune cells. A further protection is due to the presence of the maternal cumulus cells. Those cells may further prevent direct access of immune cells to the embryo. The cumulus cells persist only for the first few days after fertilization because they facilitate the fallopian tube's cilia to propagate the zygote towards the uterus. Following fertilization, it is not excluded that small proteins derived from the maternal environment, such as cytokines, will reach the zygote and early embryo. So far, there has been no evidence for such an occurrence. Following the few initial embryonic cell divisions, to the eight-cell stage, the trophoblast phase is initiated.

The trophoblast phase that occurs by the sixteen-cell stage leads to embryoblast and trophoblast differentiation. While the trophoblast's genome is principally paternally derived, the embryoblast's genome is principally maternally derived. However, since the zona pellucida still surrounds the embryo, it provides a major protection against maternal immune onslaught. Therefore, it appears that the early embryo, during the peri-implantation phase, is rather well protected from maternal immune system. This is despite the fact that the embryo is a semi-antigen. This period in in vitro fertilization/embryo transfer (IVF/ET) procedures does not occur. Consequently, the development of maternal tolerance remains permissive until implantation, which is where direct embryo/maternal contact become a necessary prerequisite.

The final preparation phase is implantation, which occurs when the embryo reaches the uterus and intimate maternal contact is initiated. During implantation the zona pellucida opens, and the trophoblast cells are extruded. This is the time that the embryo is most vulnerable. The embryo is not yet attached to the maternal surface, and it is still exposed to endometrial maternal immune cells as well as potentially hostile cytokines. Of all phases of reproduction, the implantation phase is the most crucial. Specifically, in the case of embryo transfer, following IVF, the embryo has to sojourn in the endometrial cavity for 4-5 days until the maternal organism will accept it. This is a period of endometrial priming by embryonic signaling that leads to maternal tolerance, which is the pre-requisite for successful pregnancy.

Mammalian reproduction was the last to evolve and it required a major shift in the immune system. This is because it allowed a sperm, which might be regarded as a parasite, to invade the maternal organism, and impose, in part, its own genome expression. This suggests that the embryo must have an active role in allowing the initiation of pregnancy. This suggestion is supported by the following observations:

(i) Donor embryos can implant without difficulty, therefore sharing of maternal antigens is not required;

(ii) The site of embryo implantation is not obligatory, although the uterus is preferred. Occasionally, implantation can be found in the fallopian tubes, ovaries, and even inside the abdominal cavity;

(iii) Under certain circumstances, embryos from one species can be implanted and delivered by another species. Genetic mismatch also does not prevent a successful reproduction (i.e.: mule);

(iv) Only viable embryos will implant. Therefore, the implantation is an active act that requires a passive accommodation by the maternal recipient, upon which the embryo can impose its will, in order for the pregnancy to develop;

(v) Sick mammals can also get pregnant, which indicates that the maternal organism does not need to be in good health in order for pregnancy to initiate. This reiterates the passive role of the maternal organism and supports a specific embryo effect;

(vi) The chances of multiple embryos to implant are higher than that of a single embryo. Consequently, an enhanced embryo derived signaling is likely to lead to maternal acceptance; and (vii) Although a window of opportunity for implantation does exist, it is not strict. Therefore the embryo can implant in less than favorable endometrium, as well.

In conclusion, it appears that the embryo, to a large degree, controls it own destiny. This destiny is irrespective of timing in cycle, site of implantation, the sharing of genes, species, or the health of the mother.

Early work on pregnancy suggested that shortly after fertilization, certain changes that favor tolerance take place in the maternal environment. Those changes were believed to be due to early pregnancy factor (EPF) and platelet activating factor (PAF). However, these factors are not specific to pregnancy and are found in a non-pregnant state as well. More recent work indicates that the embryo's presence, and the products that it secretes, creates a favorable and tolerant environment for a successful pregnancy. Several reports have shown that the embryo-conditioned media has immune-modulatory effects on the maternal organism. The addition of the conditioned culture media, from human and mouse embryos, affects human immune cells activity. This immune modifying activity occurs very early, at the two-cell stage embryo. The activity is dependent on embryo viability, since the media of cultured atretic eggs does not exert such immune-modulatory features. Therefore, shortly after fertilization, the embryo starts actively to emit signals that create maternal recognition of pregnancy which lead to immune tolerance. The cumulus cells, which surround the segregated embryo, may serve as a relay system, since they contain active immune cells that secrete cytokines. Such an intimate contact between putative embryo-derived compounds, and the maternal immune system, would allow for a rapid diffusion of signals from the embryo. This would lead to a local immune response, due to the embryo presence, followed by a systemic maternal immune recognition. Such changes in maternal immunity are shown via a variety of bioassays, including a pre-implantation factor (PIF) assay that measures immune changes in the maternal systemic circulation. This immune change occurs within the first few days after fertilization. Additionally, using IVF cycles, it has been shown that within three days after embryo transfer, PIF activity can be found already in maternal circulation. This indicates that embryo-initiated signaling will rapidly create a systemic immune system tolerance to the embryo. Without wishing to be bound by theory, increased PIF activity may explain why implantation does not necessarily take place in the uterus, but it can occur elsewhere within the organism, and suggest that for embryo transfer to be successful, a similar PIF signal has to exist.

SUMMARY

Embodiments of the present invention relate to biological effects induced in vitro and/or in vivo by pre-implantation factor (PIF) peptides, peptidomimetics, and compounds derived from pre-implantation embryos that harbors in part, is identical to, or is homologous to the amino acid sequence of PIF peptides or to the scrambled amino acid sequence of PIF peptides. In particular, it has not been demonstrated that a synthetic peptide comprising or mimicking the structural and biological features of the PIF-1 carboxy-terminal tetrapeptide exerts substantially similar effect on immune cells of naturally occurring PIF-1. Accordingly, this peptide and molecules that mimic the structure and function of this peptide may be used as therapeutic agents to modulate immune activity.

Thus, according to one aspect of the invention, a synthetic tetrapeptide is provided, which binds a PIF receptor and effects changes on the immune system. The synthetic tetrapeptide preferably comprises an amino acid sequence of a C-terminal sequence of a cellular PIF-1 protein. As disclosed in co-pending U.S. application Ser. No. 10/971,760 filed Oct. 22, 2004, the addition of nPIF-1$_{15}$ (SEQ ID NO:1) to stimulated PBMC caused an increase in T$_H$2 (IL10) type cytokine while reducing T$_H$1 (INF-γ) type cytokine secretion and similarly, addition of sPIF-14 (SEQ ID NO: X) to stimulated PBMC caused an increase in T$_H$2 (IL10) type cytokine while reducing T$_H$1 (INF-γ) type cytokine secretion. PIF tetrapeptides of the present invention have shown comparable activity to naturally occurring PIF peptides.

In preferred embodiments, the tetrapeptide comprises the sequence X1-X2-X-3, X-4, wherein X1 is P, X2 is G, X3 is S, and X4 is A. In other embodiments, the tetrapeptide may be supplemented with one or more of up to 11 additional amino acid residues. In preferred embodiments, the additional amino acid residues comprise a sequence the same as cellular PIF-1 proteins.

In another embodiment, a synthetic tetrapeptide that binds to a PIF receptor comprising an amino acid sequence of P-G-S-A (SEQ ID NO:19) or a peptidomimetic thereof is provided. In further embodiments, a pharmaceutical composition comprising an amino acid sequence of P-G-S-A (SEQ ID NO:19) or a peptidomimetic thereof is provided.

The invention also relates to the development of antibodies to quantitatively detect PIFs peptides in biological fluids. Including, for example, examining the presence of PIF in human embryo culture media as an index of embryo viability, detecting pregnancy, and determining human embryo viability in human and other mammalian body fluids.

A further aspect of the present invention is non-peptide or partial peptide mimetics of any of the aforementioned synthetic peptides.

In another aspect, the present invention provides for a method of assessing the quality of pregnancy in animals and humans by detecting the presence of PIF peptides, including, but not limited to PIF tetrapeptides in various tissues or fluids.

In a further embodiment, the present invention provides a method of determining endometrial receptivity in animals and humans by administering PIF peptides and derivatives thereof, including, but not limited to a PIF tetrapeptide.

The present invention further relates to generation of specific antibodies against PIF. High titer polyclonal antibodies were generated against synthetic nPIF-1$_{15}$ (SEQ ID NO:1), nPIF-2$_{13}$ (SEQ ID NO:7) and nPIF-3$_{18}$ (SEQ ID NO:10) and ELISA assays to measure PIF in biological fluids has been developed, showing differences between pregnant and non-pregnant samples for PIF-1 ELISA (SEQ ID NO:1); determining presence of pregnancy, its viability and outcome in human as well as in other mammals.

In a further aspect, the present invention provides for a method for enhancing pregnancy success by administering PIF peptides, including, for example, PIF tetrapeptides. PIF peptides modulate the immune system and do not cause basal immune suppression, could be applied to enhance pregnancy success. As shown in mouse model, increased rates of embryo implantation and fetal survival following exposure to PIF-1 (SEQ ID NO:1) was noted.

In a further aspect, the present invention provides a method of preventing or inhibiting xenotransplant rejection by administering PIF peptides, including, but not limited to PIF tetrapeptides. This is based on the observation that in the MLR system PIF-1 (SEQ ID NO:1) blocked the reaction. Further, an aspect of the present invention relates to treatment of autoimmune diseases (including, but not limited to, lupus, arthritis, and diabetes) by administering PIF tetrapeptides, where activated inappropriate immunity plays a key role. The ability to suppress that portion of the immune system that attacks various elements in the body may reduce or prevent these serious debilitating conditions.

In a further non-limiting embodiment, the present invention relates to the development of a novel non-steroid based contraceptive method by administering PIF peptides, including, PIF tetrapeptides. PIF-1 (SEQ ID NO:1) activity was blocked by scrPIF-1 (SEQ ID NO:5) both on the immune cells and the endometrium, likely acting through the same receptor, since unlabeled scrPIF-1 (SEQ ID NO:5) displaced FITC labeled PIF-1 (SEQ ID NO:1) from the receptor as well as unlabeled scrPIF-1. Therefore scrambled PIF peptides, including, but not limited to scrambled PIF tetrapeptides, could be administered to women or other mammals to prevent conception since it would not allow further embryo development, and will not interfere with the hormonal cycle. As such, the therapy could be devoid or exhibit decreased side effects that are associated with the use of current steroid based contraceptives. Data in vivo shows non-toxic contraceptive effect of scrPIF-1. The scrPIF-1 (SEQ ID NO:5), since it is an inducer of $T_H1$ activity, could have therapeutic use for stimulating the immune system in cases of immune suppression due to cancer, HIV for a non-limiting example.

The present invention also relates to the use of PIF antibodies to the PIF tetrapeptide for immunocytochemical and Western blot to identify PIF related proteins in pregnant tissues, fetus and placenta. This allows identifying pregnancy pathologies like premature labor and growth restriction as non-limiting examples. In addition, such PIF peptides may exhibit differential expression in various stages of gestation.

In a further embodiment, PIF antibody may determine differential expression of PIF in fetal organs, like liver and spleen, and suggest that PIF may block graft-versus-host disease by their local action (preventing activation of fetal immune system until delivery). The PIF antibodies used as affinity column can identify associated functional proteins in pregnant tissues as seen by identification of several distinct proteins in the term placenta. In such an embodiment, other biomarkers can be identified that may be modified by pregnancy disorders. Identification of these proteins allow the examination of the genes that are associated with these proteins highly relevant for blastocyst development. These proteins using mass spectrometry or antibodies can also aid together with PIF peptides, including tetrapeptides, to determine embryo viability following in vitro fertilization thereby increasing the chances for pregnancy following transfer.

DESCRIPTION OF THE DRAWINGS

The file of this patent contains at least one drawing executed in color. Copies of this patent with color drawing(s) will be provided by the Patent and Trademark Office upon request and payment of the necessary fee.

In part, other aspects, features, benefits and advantages of the embodiments of the present invention will be apparent with regard to the following description, appended claims and accompanying drawings where:

FIG. 5A: sPIF-$1_{(15)}$ (SEQ ID NO: 13) ELISA standard curve PIF antibody detects low sPIF levels (pg). Polyclonal antibodies AbPIF-$1_{(15)}$ were generated against sPIF-$1_{(15)}$ (SEQ ID NO:13) in rabbits (Covance Inc.). High titers 50% at 1:50,000 were achieved. Serial dilutions of synthetic sPIF-$1_{(15)}$ (SEQ ID NO:13) were plated, blocked and then washed off. PIF-1 antibody (1:5000) was added incubated and washed off. Goat anti-rabbit antibody was added, incubated and washed off. Reaction was stopped by SDS and counted in plate reader (Biosynthesis Inc, G Vandydriff). The antibody affinity was also confirmed by using a competition analysis between biotin labeled and unlabeled sPIF-$1_{(15)}$ (SEQ ID NO:13) (data not shown). Also, when scrPIF-1 (SEQ ID NO 5) was tested in the assay, the antibody did not recognize it attesting to the high specificity of the antibody that was generated. Similar dose dependent results in the ELISA were obtained with affinity purified PIF-2 and PIF-3 antibodies (dilutions of the antibody up to 25,600) with linearity to the 30 pM of the peptide (data not shown).

FIG. 15. Placenta staining of PIF-1 in the second trimester with premature labor (5 placentas). Indicates PIF-1 disappears from the placenta with premature labor.

FIG. 19. FITC-PIF-1 binds to spleen in vivo IV injected mice, also pick up in the bone marrow, slower pickup in the cecum, rapid elimination by the kidney.

FIG. 20. PIF ELISA of PIF-1 using PIF-1 IgG v. control and PIF-1 Mab.

DETAILED DESCRIPTION

Figure 1:
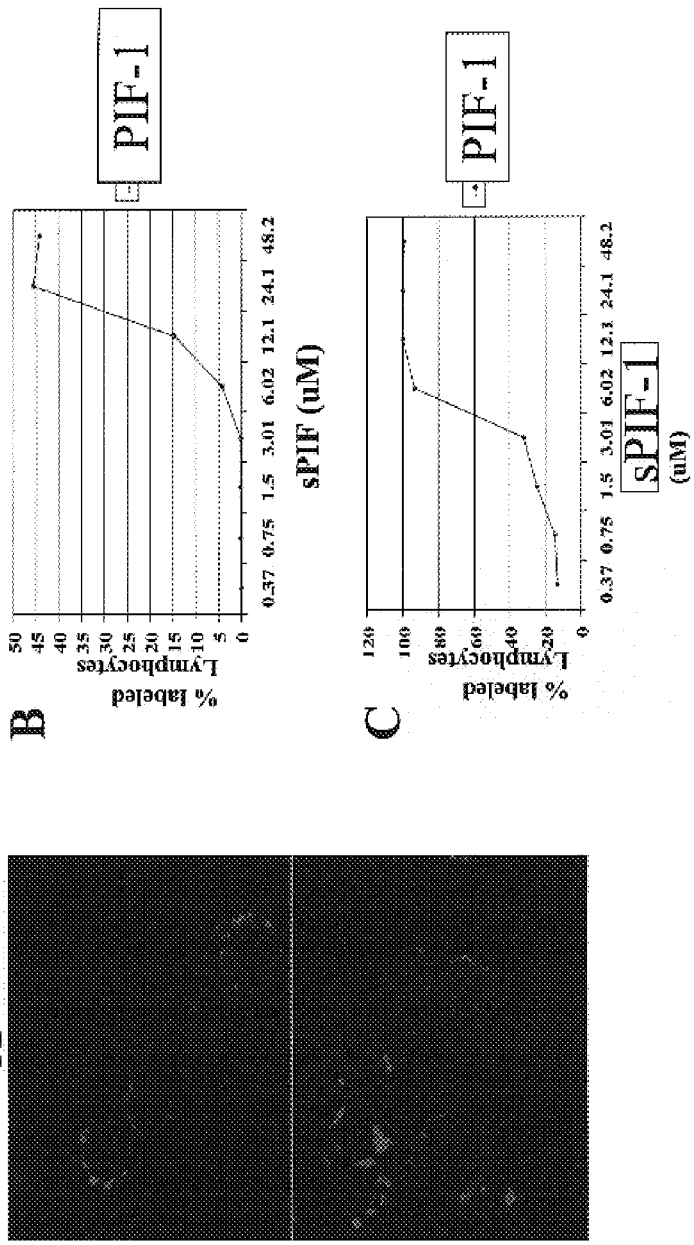
FIG. 1 shows that sPIF-$1_{(15)}$ (SEQ ID NO:13) binds to PBMC, which forms rosettes in their P-L assay. (A) Fluorescence-labeled sPIF-$1_{(15)}$ (SEQ ID NO:13) binding to human Lymphocytes in a dose dependent manner. (B) Binding of FITC sPIF-$1_{(15)}$ (SEQ ID NO:13) to the total PBMC population (C) Binding to lymphocytes that form rosettes with platelets, P-L bioassay, documents presence of nPIF-$1_{(15)}$ (SEQ ID NO:1) receptors on the PBMC surface.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

The terms "effective amount" or "therapeutically effective amount" is an amount sufficient to decrease or prevent the symptoms associated with a medical condition or infirmity, to normalize body functions in disease or disorders that result in impairment of specific bodily functions, or to provide improvement in one or more of the clinically measured parameters of a disease or disorder.

"Treatment" refers to the administration of medicine or the performance of medical procedures with respect to a patient, for either prophylaxis (prevention), to cure the infirmity or malady in the instance where the patient is afflicted refers, or amelioration the clinical condition of the patient, including a decreased duration of illness or severity of illness, or subjective improvement in the quality of life of the patient or a prolonged survival of the patient.

The terms "patient" and "subject" mean all animals including humans. Examples of patients or subjects include humans, cows, dogs, cats, goats, sheep, and pigs.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

The PIF assay, as disclosed in U.S. Pat. No. 5,646,003 to Barnea et al., entitled "Preimplantation Factor" issued Jul. 9, 1997, and in U.S. Pat. No. 5,981,198 to Barnea et al., entitled "Preimplantation Factor" granted Nov. 9, 1999, the disclosures of which are incorporated herein by reference in their entirety, may be used to measure the response of the immune system to pregnancy specific preimplantation factors. Studies employing the PIF assay for culture media of human or mouse embryos that were grown, show that PIFs were able to increase the in-vitro formation of rosettes between donor lymphocytes and platelets in the presence of monoclonal anti-CD2 (type T11-1). Lymphocyte-platelet rosettes result from the interaction of the T cell surface protein CD2 with its ligand CD58 expressed on the platelet membrane. Anti-CD2, by binding to the CD2 antigen on the T cells, inhibits their interaction with platelets. However, the embryo-derived factor(s), PIFs, present in the culture medium or pregnant peripheral sera appears to counteract this inhibition. The PIF activity was already apparent in the viable two-cell stage embryo. Thus both of those compounds properties are very likely to be similar. This observation strongly suggests that there are several putative compounds that may be very potent, and create an environment that is favorable for pregnancy.

Using this assay, it has been determined that the presence of PIF activity in maternal serum within four days after embryo transfer indicates a >70% chance of successful pregnancy outcome. In contrast, absence of PIF activity indicated that pregnancy would not develop in 97% of cases. PIF is detectable 5-6 days after intrauterine insemination and is absent in non-pregnant serum and in culture media of non viable embryos, present in the sera of various mammals including horse, cow, pig and humans. Without wishing to be bound by theory, the PIF assay results indicate that if the embryo is able to secrete these immunomodulatory PIF compounds, it is capable of implanting and achieving a good pregnancy outcome. The importance of PIF as a marker of a good quality pregnancy is further illustrated by the fact that if a pregnancy ends in miscarriage, the PIF activity progressively declines until it reaches non-detectable levels. In contrast, in the case of a poor quality pregnancy, Human Chronic Gonadotropin (hCG) levels do not change significantly for the next 3 weeks until the miscarriage is clinically evident.

PIF activity is found in several mammalian species, including humans, horse, cow, pig, and mouse and sheep. Human immune cells used for the PIF assay (homologous lymphocytes and platelets) interacted well with the human sera, as well as with sera from different species and embryo culture media. This cross-species interaction indicates that similar compounds are involved in the different species. PIF activity is due to the presence of similar low molecular weight peptides, both in mouse embryo culture media and in pregnant porcine serum. A PIF assay was used as a test to identify and characterize the PIF related compounds within a conditioned mouse embryo culture media. Using a multi-step chromatographic technique, coupled with the PIF bioassay, a group of a putative PIF embryo derived peptides with 9-18 amino acids in length were identified and sequenced. These sequences are disclosed in PCT/US02/20599 to Barnea et al., entitled "New Assays for Preimplantation Factor and Preimplantation Peptides," filed Jun. 28, 2002, the contents of which are incorporated herein by reference in their entirety. Based on the sequences derived, synthetic peptides were generated.

The first natural PIF compound identified, termed nPIF-$1_{(15)}$ (SEQ ID NO:1), is a 15 amino acid peptide. A synthetic version of this peptide, sPIF-$1_{(15)}$ (SEQ ID NO:13), showed activity that was similar to the native peptide, nPIF-$1_{(15)}$ (SEQ ID NO:1). This peptide is homologous to a small region of the Circumsporozoite protein, a malaria parasite. The second PIF peptide, nPIF-$2_{(13)}$ (SEQ ID NO:7), includes 13 amino acids and shares homology with a short portion of a large protein named thyroid and retinoic acid transcription co-repressor, which is identified as a receptor-interacting factor, (SMRT); the synthetic version is sPIF-2 (SEQ ID NO:14). The third distinct peptide, nPIF-$3_{(18)}$ (SEQ ID NO:10), consists of 18 amino acids and matches a small portion of reverse transcriptase; the synthetic version of this peptide sPIF-$3_{(18)}$ is (SEQ ID NO:15). nPIF-$4_{(9)}$ (SEQ ID NO:12) shares homology with a small portion of reverse transcriptase.

Further synthetic peptides were generated based upon sequences of naturally occurring PIF-1 peptides. In particular, derivatives of PIF-1 peptides were generated, including, for example PIF-$1_{(4)}$ (SEQ ID NO: 19) and PIF-$1_{(5)}$ (SEQ ID NO: 18).

One aspect of the present invention provides a composition comprising a synthetic PIF peptide and an excipient. In further embodiments, the synthetic PIF peptide is a PIF tetrapeptide, preferably corresponding to the amino acid sequence of SEQ ID NO:19. In further embodiments, the PIF tetrapeptide may comprise additional amino acid residues, up to an additional 11 amino acids. In preferred embodiments, the PIF tetrapeptide may comprise additional amino acid residues corresponding to the amino acid sequence of SEQ ID NO:1, SEQ ID NO:3, SEQ ID NO:4, SEQ ID NO:13, SEQ ID NO:16, or SEQ ID NO:19.

In one embodiment, the PIF peptides of the present invention are modified to produce peptide mimetics by replacement of one or more naturally occurring side chains of the genetically encoded amino acids (or D amino acids) with other side chains, for instance with groups such as alkyl, lower alkyl, cyclic 4-, 5-, 6-, to 7 membered alkyl, amide, amide lower alkyl, amide di (lower alkyl), lower alkoxy, hydroxy, carboxy and the lower ester derivatives thereof, and with 4-, 5-, 6-, to 7 membered heterocyclics. For example, proline analogs can be made in which the ring size of the proline residue is changed from 5 members to 4, 6, or 7 members. Cyclic groups can be saturated or unsaturated, and if unsaturated, can be aromatic or nonaromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. I-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, Ann. Rep. Med. Chem. 24, 243-252, 1989). Certain peptidomimetic compounds are based upon the amino acid sequence of the peptides of the invention. Often, peptidomimetic compounds are synthetic compounds having a three-dimensional structure (i.e. a "peptide motif") based upon the three-dimensional structure of a selected peptide. The peptide motif provides the peptidomimetic compound with the desired biological activity, i.e., binding to PIF receptors, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art (see, e.g., Ripka & Rich, Curr. Op. Chem. Biol. 2, 441-452, 1998; Hruby et al., Curr. Op. Chem. Biol. 1, 114-119, 1997; Hruby & Balse, Curr. Med. Chem. 9, 945-970, 2000). One class of peptidomimetics a backbone that is partially or completely non-peptide, but mimics the peptide backbone atom-for atom and comprises side groups that likewise mimic the functionality of the side groups of the native amino acid residues. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

In a further embodiment, a compound of the formula $R_1$-$R_2$-$R_3$-$R_4$ is provided, wherein $R_1$ is Pro or a mimetic of Pro, $R_2$ is Gly or a mimetic of Gly, $R_3$ is Ser or a mimetic of Ser, and $R_4$ is Ala or a mimetic of Ala. In alternative embodiments, the compound may comprise one or more of up to 11 additional amino acid residues.

Without wishing to be bound by theory, present evidence suggests that both within the embryos immediately surrounding (found in the fallopian tube, and endometrium in vivo), and in the peripheral circulation, similar PIF peptides may be responsible for both the immune effects, and for the creation of a pro-pregnancy environment.

Considerable evidence exists that impaired maternal immune tolerance to the semi-allogeneic conceptus is a cause of implantation failure and pregnancy loss. The distribution of T-helper cell ($T_H$) sub-populations and the resulting local and systemic cytokine balance may play an important role in pregnancy viability. Following antigenic stimulation, $T_H$ cells respond by differentiating into one of two cell types: $T_H1$ which produces mainly interleukin 2 (IL-2) and interferon γ (IFN-γ) as well as tumor necrosis factor a (TNF-α); and $T_H2$, which produces IL-4, IL-5 and IL-10. $T_H$-specific cytokines tend to both stimulate proliferation of the $T_H$ cell subset from which they are derived and inhibit development of the opposite $T_H$ cell subset. $T_H1$ cells are involved in cell-mediated immune reactions while $T_H2$ cells are involved in humoral immunity. A predominance of $T_H2$ cytokines is found in normal pregnancies, and IL-4 and IL-10 released by these cells appear to support pregnancy. In contrast, the $T_H1$ cytokines, IL2, IFN-γ and TNF-α are associated with reproductive failure in both humans and mice. However both types of cytokines are required to maintain pregnancy, since the maternal system must be able to fight against infection while tolerating the fetus. It has been postulated that the pre-implantation embryo may play a role in protecting itself from maternal immune rejection by secretion of factors that would promote the shift of $T_H$ cells towards the $T_H2$ phenotype. These PIF compounds may be to be used for treatment of inflammatory or other immunological diseases, and preferably the drug or biological is derived from—or its structure is based on the structure of the circumsporosoite protein of malaria.

In one embodiment, embryo-derived compounds, PIF peptides, including, but not limited to PIF tetrapeptides, or peptidomimetics thereof, can be used for both diagnosis and therapy. Non-limiting examples of the effects of such PIF peptides include modulation of the immune system while not causing basal immune suppression, and use of PIF peptide to enhance endometrial receptivity. Such methods of treatment may involve increased expression of endometrial receptivity markers, including, but not limited to beta 3-integrin.

In another embodiment, a method of detecting a PIF peptide is provided. The PIF peptide may include, for example, SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID No. 18 or SEQ ID NO. 19. In a further embodiment, a method of detecting a PIF peptide which includes a fragment of $nPIF-1_{(15)}$, $nPIF-2_{(13)}$, $nPIF-3_{(18)}$ or $nPIF-4_{(9)}$, including, but not limited to $sPIF-1_{(4)}$ (SEQ ID NO. 19).

The PIF peptides and peptidomimetics of the present invention may be coupled to produce labeled peptides, for example but not limited to FITC, biotin, rhodamine, radioactive labels, fluorescent nanocrystals, and other labels known to those skilled in the art, that may be used to identify PIF receptor sites present on immune cells, endometrium, on the embryo itself, as well as elsewhere within the body where PIF peptides specifically bind.

Embodiments of the present invention may be used to identify and clone the genes that are responsible for PIF peptides expression. cDNA library is prepared from human placenta (Invitrogen) that have libraries of 1-2.5 kb size inserts which represent even the rarest sequences. Oligonucleotides are generated based on the peptides sequences and are probed against the cDNA library using plate screening procedures. The PIF peptides presence in the placenta was previously documented using immunohistochemical techniques by labeled PIF-1 and PIF-3 antibody. The species of PIF peptides present in the placenta are confirmed with affinity purified and labeled PIF-1, PIF-2, and PIF-3 antibodies using a Western blot. The present invention may be used to generate specific antibodies polyclonal and monoclonal for assay development to measure PIF levels and activity in biologic fluids and tissues such as but not limited to serum, blood, urine, milk, and saliva as well as embryo culture media, gestational tissue, and fetal tissue.

Embodiments of the present invention include those peptides derived from pre-implantation embryos that induces $T_H2$ type cytokines like IL-10 synthesis or secretion from lymphocytes or other white blood cells and pharmacophores that binds specifically to PIF receptors (such but not limited to PGSA, AVRIKPGSANKPSDD (SEQ ID NO: 20), VRIKPGSANKPSDD (SEQ ID NO: 21) or QVRIKPGSANKPSDD (SEQ 11D NO: 22)) or by substituting with D amino acids or by adding PEG. Preferably such peptides are from pre-implantation embryos and increases $T_H2/T_H1$ ratio through increased number of lymphocytes containing the desired cytokines and/or by preferential secretion of $T_H2$ over $T_H1$ cytokines into the media. Such pre-implantation embryo-derived peptide may be used to cause a shift from pro-inflammatory to anti-inflammatory activities in lymphocytes.

In a further embodiment isolated or synthetic PIF peptides may be used in a method of identifying cellular or tissue binding sites for PIF peptides in a patient, the method comprising administering labeled PIF peptides, including, but not limited to PIF tetrapeptides, to said tissue and detecting the label. The binding sites may include, for example, immune cells, endometrial cells, epithelial cells, gestational tissues, embryos and the like.

In another embodiment, a method of identifying PIF receptors on cells is provided. The method may involve combining labeled PIF peptides, including, but not limited to PIF tetrapeptides, with activated immune cells membranes and further detecting the presence of labeled PIF peptides on activated cells or on other target organs, including, but not limited to spleen, liver, bone marrow and the endometrium.

PIF peptides or peptidomimetics may be used to treat a patient by administering a therapeutic amount of one or more PIFs to create tolerance for an embryo and therefore pregnancy acceptance by the female to maintain pregnancy until term. In this embodiment, PIF peptides, including, but not limited to PIF tetrapeptides, can be used for the treatment of infertility disorders and for the enhancement of pregnancy. Other non-limiting examples where such PIF peptides may be used include preventing miscarriage and premature labor in mammals such as women, farm, and non-farm animals. The PIF peptides, tetrapeptides, peptidomimetics or compositions thereof may be administered using transdermal methods including patch, by injection, or pill, and may include liposome or carbohydrate coated formulations, for example.

In another non-limiting embodiment, PIF peptides may be added to embryo culture media in order to enhance the ability of the transferred embryos to implant thereby reducing the number of embryos that are needed in order to have a high rate of implantation, and successful pregnancy. PIF could also enhance embryonal viability by acting in an autocrine manner on the embryo itself. In such embodiments, the PIF peptide may comprise, PIF tetrapeptides, such as sPIF-$1_{(4)}$ (SEQ ID NO:19).

In further embodiments, methods of involving compounds of pre-implantation embryo origin that decrease or modify the $T_H1/T_H2$ ratio are used as drugs (biologics) to improve the immune system of the mother to be able to better receive the embryo, as a treatment of infertile women (parenterally or as a co-additive to the embryo cultures in the ET procedure) are provided. In such a method, a therapeutically effective amount of PIF peptide or tetrapeptide is administered in vivo or in vitro. In certain embodiments, the PIF peptides may be administered prior to, during and/or after implantation of the embryo.

Pre-implantation embryo origin compounds or analogs may be used in procedures that decrease or modify the $T_H1/T_H2$ ratio in lymphocytes. In these procedures the PIF peptides may be used to treat immunological diseases that benefit from a reduction in the pro-inflammatory activity or enhancement of anti inflammatory activity of the immune system in animals and humans. Alternatively, these compounds and their analogs can block a decrease or modification in the $T_H1/T_H2$ ratio in lymphocytes to treat immunological diseases where antibodies are over-produced and inhibition thereof is beneficial in humans and animals. For example, PIF tetrapeptides or peptidomimetics may be administered to non-pregnant patients that have autoimmune diseases like lupus and rheumatoid arthritis where the aim is to reduce the rate of activated immunity while maintaining the basal immunity that is required for defense of the organism. In another non-limiting example, the PIF tetrapeptides may decrease or modify the $T_H1/T_H2$ ratio in lymphocytes are used to control the function of other proteins that do same effects (e.g. Progesterone Induced Blocking Factor). The administration can be made through non-limiting examples such as a patch, injection, or pill form.

In a further embodiment, a PIF-based pregnancy diagnosis is provided. In one non-limiting embodiment, the diagnosis may be obtained utilizing an ELISA or yes/no stick in the form of a kit. The components of the PIF ELISA kit may include, for example, HRP-Avidin, PIF-Biotin and PIF antibody. In the absence of PIF in the test sample, HRP enzyme would bind to the antibody through the PIF-biotin complex, generating a maximum color. In the presence of PIF in the test sample, PIF binds to the PIF antibody and prevents the HRP enzyme complex from binding, generating a minimum color.

Another embodiment of the present invention provides for a method of identifying the site of action, the cell receptors, to which PIF peptides have to bind in order to exert their biological effects. This binding may be on immune cells, endometrium, spleen, liver or elsewhere in the organism, including the embryo or placenta itself. The method may include administering a labeled PIF tetrapeptide and further detecting the labeled PIF tetrapeptide. Further embodiments provide for a composition for identifying PIF receptor sites comprising a PIF tetrapeptide and a label. The label may include, for example, FITC, biotin, rhodamine, radioactive isotopes and fluorescent labels, such as nanocrystals. A further embodiment includes isolation and cloning of these receptors. cDNA library of PBMC (Invitrogen) is used for expression screening. Binding of PIF-1,2,3 (FITC) to COS-M6 cells is examined and positive clones are sequenced. The method for direct identification of PIF receptor on PBMC and endometrium may be carried out using affinity column with Biotin labeled PIF-1, PIF-2, PIF-3 or PIF-4 and passage of mitogen stimulated PBMC enriched membrane preparation, followed by mass spectrometry analysis and sequencing. Alternatively, using mitogen stimulated PBMC followed by mRNA extraction followed by analysis with Affymetrix total gene chip. mRNA up-regulated by about 30% or more or down-regulated by about 30% or more are amplified and verified by PCR. This method also provides for identifying the intracellular mechanisms including the transcription factors that lead to the changes noted in cytokines secretion but not limited to the immune system's function. Also the method allows for the identification of the secretory products, such as but not limited to cytokines, and growth factors, that are modified following exposure to the PIF tetrapeptides. This may be accomplished by determined dependence of PIF-1, PIF-2, PIF-3 and PIF-4 on calcium channels using Flex station of K channels and determining dependence on PKC, calcineurin, or NFAT, among others, as well as dependence upon intracellular kinases, transcriptimoses and metabolomics.

Another embodiment of the present invention provides for making polyclonal or monoclonal antibodies that were raised against PIF. In one non-limiting embodiment, polyclonal or monoclonal antibodies may be raised against PIF in mice and rabbits. In another embodiment, antibodies to PIF may be created by providing a hybridoma cell that produces a monoclonal antibody specific for a PIF peptide and culturing the cell. In preferred embodiments, the antibodies are raised against PIF tetrapeptides, for example sPIF-$1_{(4)}$ (SEQ ID NO:19).

Such antibodies provide a method for determining the presence of PIF levels in samples by using but not limited to ELISA, EIA, lateral flow assay, microfluidics or mass spectometry. Such a method and antibodies may allow precise measurements of PIF levels in fluids such as but not limited to maternal blood, urine, saliva, milk, and embryo culture media and gestational tissues. The method is applicable for all PIF peptides and may be used to provide an early diagnostic method that reflects pregnancy and its viability in various patients starting at the pre-implantation period. The patients may include women, to monitor results of infertility therapy and pregnancy well being, as well as other mammals, including farm and non-farm animals, and non-mammals. In the embryo culture media, the ELISA assay using such antibodies provides a method for assessing the presence of PIF peptides to assess embryo viability before transfer. Various aspects of the present invention will be illustrated with reference to the following non-limiting examples.

TABLE 1

PIF Peptides

| SEQ ID NO | Peptide | Amino Acid Sequence |
|---|---|---|
| SEQ ID NO: 1 isolated native, matches region of Circumsporozoite protein (Malaria) | nPIF-1$_{15}$ | MVRIKPGSANKPSDD |
| SEQ ID NO: 2 isolated native, matches region of Circumsporozoite protein (Malaria) | nPIF-1$_{(15\ alter)}$ | MVRIKYGSYNNKPSD |
| SEQ ID NO: 3 isolated native, matches region of Circumsporozoite protein (Malaria) | nPIF-1$_{(13)}$ | MVRIKPGSANKPS |
| SEQ ID NO: 4 isolated native, matches region of Circumsporozoite protein (Malaria) | nPIF-1$_{(9)}$ | MVRIKPGSA |
| SEQ ID NO: 5 synthetic, scrambled amino acid sequence from region of Circumsporozoite protein Malaria | scrPIF-1$_{15}$ | GRVDPSNKSMPKDIA |
| SEQ ID NO: 6 isolated native, matches region of human retinoid and thyroid hormone receptor-SMRT | nPIF-2$_{(10)}$ | SQAVQEHAST |
| SEQ ID NO: 7 isolated native, matches region of human retinoid and thyroid hormone receptor (SMRT) | nPIF-2$_{(13)}$ | SQAVQEHASTNMG |
| SEQ ID NO: 8 synthetic, scrambled amino acid sequence from region of human retinoid and thyroid hormone receptor SMRT | scrPIF-2$_{(13)}$ | EVAQHSQASTMNG |
| SEQ ID NO: 9 | scrPIF-2$_{(14)}$ | GQASSAQMNSTGVH |
| SEQ ID NO: 10 isolated native, matches region of Rev Trans | nPIF-3$_{(18)}$ | SGIVIYQYMDDRYVGSDL |
| SEQ ID NO: 11 synthetic, scrambled amino acid sequence from region of Circumsporozoite protein Malaria | Neg control for negPIF-1$_{(15)}$ | GMRELQRSANK |
| SEQ ID NO: 12 isolated native, matches region of Rev Trans | nPIF-4$_{(9)}$ | VIIIAQYMD |
| antibody of native isolated nPIF-1$_{15}$ | AbPIF-1$_{(15)}$ | |
| SEQ ID NO: 13 | sPIF-1$_{(15)}$ | MVRIKPGSANKPSDD |
| synthetic, amino acid sequence from region of Circumsporozoite protein Malaria | | |
| SEQ ID NO: 14 synthetic, amino acid sequence from of human retinoid and thyroid hormone receptor SMRT | sPIF-2$_{(13)}$ | SQAVQEHASTNMG |
| SEQ ID NO: 15 synthetic, amino acid sequence from region of Circumsporozoite protein Malaria | sPIF-3$_{(18)}$ | SGIVIYQYMDDRYVGSDL |
| SEQ ID NO: 16 synthetic, amino acid sequence from region of Circumsporozoite protein Malaria | sPIF-1$_{(9)}$ | MVRIKPGSA |
| antibody of native isolated nPIF-2$_{(13)}$ | AbPIF-2$_{(13)}$ | |
| antibody of native isolated nPIF-3$_{(18)}$ | AbPIF-3$_{(18)}$ | |
| SEQ ID NO: 17 synthetic | sPIF-4$_{(9)}$ | VIIIAQYMD |
| SEQ ID NO: 18 synthetic | sPIF-1$_{(5)}$ | MVRIK |
| SEQ ID NO: 19 synthetic | sPIF-1$_{(4)}$ | PGSA | n = native, s = synthetic, scr = scrambled, same AA, ( ) = number of AA, Ab = antibody Preimplantion factor peptides were synthesized by solid-phase peptide synthesis (SPPS, Applied Biosystems Peptide Synthesizer, Model 433) employing Fmoc (9-fluorenyl-methoxycarbonyl) chemistry in which the a-amino nitrogen of each amino acid is blocked with Fmoc. Upon completion of the synthesis, final purification is carried out by reversed-phase HPLC and identity is verified by MALDI-TOF mass spectrometry and amino acid analysis. sPIF-1$_{15}$ (SEQ ID NO:13) and scrPIF-1$_{15}$ (SEQ ID NO:5) scrambled peptide (GRVDPSNKSMPKDIA) and an irrelevant 11 amino acid negative control peptide negPIF-1$_{(15)}$ (SEQ ID NO: 11) (GM-RELQRSANK) containing a similar carboxyl-terminal sequence, were synthesized. Peptides were labeled on their N-termini with fluorescein isothyocyanate (FITC) in the solid phase. A spacer group (b-alanine) was inserted between the fluorophor and the peptide. sPIF-1$_{15}$ (SEQ ID NO:13) was also labeled by adding Lysine at the C terminal. In addition, SMRT (SQAVQEHASTNMG) sPIF-2$_{(13)}$ (SEQ ID NO: 14), FITC and Biotin labeled were generated on the N terminal. Scrambled SMRT, scrPIF-2$_{(14)}$ (SEQ ID NO: 9), GQAS-SAQMNSTGVH; scrPIF-2$_{(13)}$ (SEQ ID NO: 8), EVAQH-SQASTMNG; and SGIVIYQYMDDRYVGSDL peptide (reverse transcriptase homologue—RTH) sPIF-3$_{(18)}$ (SEQ ID NO:15) were also generated synthetically.

While the present invention is described with reference to PIF's derived from mammals like mice or humans, it is to be understood that the invention is not limited to these peptides. For example, PIF peptides or their antagonists which are cloned, synthesized, or isolated from mammals like horses, cows, or swine or substituted variants of these peptides may be used in the practice of various embodiments of the present invention. It is also contemplated that substitutions of amino acids in the peptide sequence of these PIFs can be made and used as would be known to those skilled in the art in the practice of various embodiments of the present invention. Such PIF variants may be characterized by their ability to alter the $T_H1/T_H2$ ratio of antigen stimulated cells or by their ability interact with PIF receptors on cells.

PIF-1 Peptides Enhance Rosettes Formation

FIG. 1 shows that sPIF-1$_{(15)}$ (SEQ ID NO: 13), binds to PBMC, which forms rosettes in their P-L assay. FIG. 1(A) depicts fluorescence-labeled sPIF-1$_{(15)}$ (SEQ ID NO: 13) binding to human lymphocytes in a dose dependent manner. FIG. 1(B) shows binding of FITC nPIF-1$_{(15)}$ (SEQ ID NO: 1) to the total PBMC population and FIG. 1(C) shows binding to lymphocytes that form rosettes with platelets, P-L bioassay, documents presence of nPIF-1$_{(15)}$ (SEQ ID NO: 1), receptors on the PBMC surface.

Human PBMC were isolated by the Ficoll method. FITC-labeled nPIF-1$_{15}$ (SEQ ID NO: 1) and (FITC)-labeled scrPIF-1 (SEQ ID NO:5) and match-size irrelevant peptide (FITC)-labeled negative controls negPIF-1$_{(15)}$ (SEQ ID NO:11), were dissolved in PBS at concentrations ranging from 0.75 to 48.19 µM, and were incubated with 500,000 lymphocytes for 1 h at room temperature. The cells were washed 6 times with PBS and resuspended in 500 µl of the same buffer. T-cells and monocytes identification was performed in independent experiments by incubation with anti-CD3 and anti-CD14 antibody-phycoerithryn (PE) labeled. nPIF-1$_{15}$ (SEQ ID NO: 1) binding to PBMC was determined by flow cytometry. In addition, rosettes formed by T cell-platelets were detected by flow cytometry using anti-CD3 antibody-PE and anti-CD41a antibody-FITC (all antibodies were from Pharmingen Inc.). These rosettes were not labeled by the control peptides (FITC)-labeled scrPIF-1$_{(15)}$ (SEQ ID NO:5) and match-size irrelevant peptide (FITC)-labeled negative controls negPIF-1$_{(15)}$ (SEQ ID NO:11). This indicates that both embryo culture media and serum contain similar peptides and provides evidence for the utility of biologic effects of the peptides and for the diagnostic potential using antibodies against the same.

The biological characteristics of preimplantation factors in vitro were determined employing the synthetic versions of both 15-residue sPIF-1$_{15}$ (SEQ ID NO: 13) and 9-residue sPIF-1$_{(9)}$ (SEQ ID NO: 16) isoforms, which exhibit similar biological activities in vitro. Flow cytometric determination of lymphocyte/platelet rosette formation shows that both sPIF-1$_{15}$ (SEQ ID NO: 13) and sPIF-1$_{(9)}$ (SEQ ID NO: 16) isoforms induce a four-fold increase in the number of rosettes in the presence of the anti-CD2 antibody (data not shown), demonstrating that they exhibit the same anti-CD2-blocking effect manifested by the embryo-conditioned culture medium and maternal serum.

In a further example, PIFs effect on PIF bioassay and flow cytometry was observed. Compared to control, the addition of PIF increased platelet/lymphocyte rosette formation as follows:

TABLE 2

| PIF | Increase in Rosette Formation |
|---|---|
| 1 nM | >370% |
| 10 nM | >288% |
| 100 nM | >208% |

Results indicate that synthetic PIF replicates the effects seen by pregnant serum and embryo culture media results.

PIF-1 Immune Effects

Human PBMC were isolated and cultured for 2-4 days in AIM-V medium containing 0 to 200 nM of sPIF-1$_{15}$ (SEQ ID NO:13) or scrPIF-1$_{15}$ (SEQ ID NO:5). The following proliferation-activating agents were used: anti-CD3 antibody (10 µg/ml solution) bound on the plate wells in the presence or absence of IL-2 at 10 µg/ml; phytohemmaglutinin (PHA) at 4 µg/ml. The effects of sPIF-1$_{15}$ (SEQ ID NO:13) or scrPIF-1$_{15}$ (SEQ ID NO:5) peptides were also determined by the mixed lymphocyte reaction (MLR) after 3 days in heterologous cultures of PBMC with cells previously treated with mitomycin C (100 µg/ml for 4 h). Cell proliferation was determined by tritiated thymidine incorporation (16 h) of 72-h culture. Cytokine release (IL-4, IL-10, IFN-γ and TNF-α) into culture supernatants was determined at 72 h of culture by ELISA (R&D System).

Figure 2:
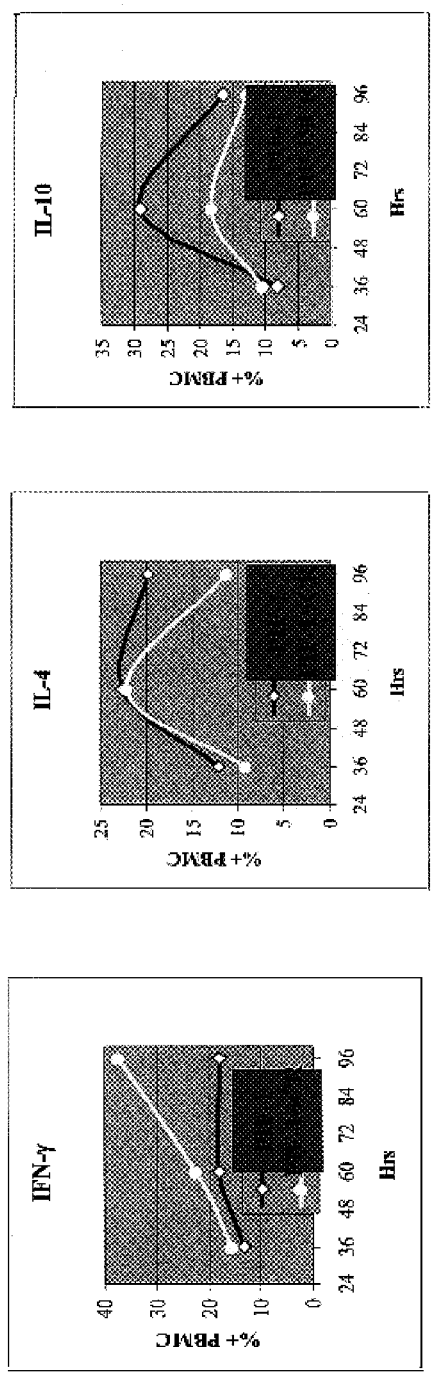
FIG. 2. sPIF-$1_{(15)}$ (SEQ ID NO:13) increases the percentage of PBMC that contain $T_H2$ type cytokines (IL10, IL 4), while scrPIF-$1_{(15)}$ (SEQ ID NO: 5) has a $T_H1$ bias (INF-gamma). Isolated PBMC were stimulated by PHA (1 ug/ml) and cultured 2-4 days with sPIF-$1_{(15)}$ (SEQ ID NO:13) or scrPIF-$1_{(15)}$ (SEQ ID NO:5). 30 nM. PBMC cytokines content was determined by specific staining using flow cytometry. Effect of PIF-1 on cellular content of cytokines of PBMC was examined up to 96 hours and a time dependent pattern emerged, not replicated by scrambled or irrelevant peptide. Measurements were carried out in two separate stages. At the cellular induction/synthetic level, lymphocytes were cultured in the presence of PHA for various periods with or without PIF-1 then processed for intracellular immunostaining (activation by PMA plus ionomycin in the presence of monenisn and berfeldin, followed by permeabilization and immunostaining) for the detection of nascent cytokines. The cytokine profile of the cells treated with PIF, showed an increase IL10 and IL4 with minimal change in IFN γ.

As shown in FIG. 2, overall sPIF-1$_{15}$ (SEQ ID NO:13) decreases the proliferation rate of human lymphocytes stimulated with diverse reagents and provokes a shift toward a $T_H2$ cytokine phenotype. sPIF-1$_{15}$ (SEQ ID NO:13) negatively affects the proliferation of activated lymphocytes. Lower rates of lymphocyte proliferation was found at 250, 62.5 and 1 nM of sPIF-1$_{15}$ (SEQ ID NO:13) for PHA, anti-CD3 antibody and MLR, respectively. The results were compared with CD3 antibody stimulated lymphocytes without sPIF-1$_{15}$ (SEQ ID NO:13) or with scrPIF-1$_{15}$ (SEQ ID NO:5) used as controls. IL-10 release is significantly increased in the culture supernatants and IFN-γ release is significantly decreased by exposure to sPIF-1$_{15}$ (SEQ ID NO:13). In contrast, sPIF-1$_{15}$ (SEQ ID NO:13) does not have a significant effect on IL-4 or TNF-α release As show in Table 3, sPIF-1$_{15}$ (SEQ ID NO:13) increases the $T_H2/T_H1$ cytokine ratio in PBMC more than five-fold, owing mainly to the substantial increase of IL-10 coupled with a decrease in IFN-γ. Number of IL-10 secreting cells also increased (50-60% starting at day 2 and peaking at days 3-4 and preceding the IFN-γ decreases (30%) by one day, suggesting that a causal relationship is likely in place with respect to the dynamics of these cytokines, as shown in FIG. 2. In contrast, same concentrations of scrPIF-1$_{15}$ (SEQ ID NO:5) had no effect, as demonstrated by intracellular staining and flow cytometry (FIG. 2).

These results demonstrate that sPIF-1$_{15}$ (SEQ ID NO: 13) has immunomodulatory effects that may lead to the development of an immune environment that is favorable to or at least tolerant for the presence of the early embryo. The $T_H2/T_H1$ cytokine ratio was determined at different concentrations of sPIF-1$_{15}$ (SEQ ID NO: 13). Similar dose dependent results at the 1-500 nM range were found in PHA and MLR activated lymphocytes by effects of sPIF-1$_{15}$ (SEQ ID NO: 13) and sPIF-1$_{(9)}$ (SEQ ID NO: 16). Similar results were obtained with sPIF-2 (SEQ ID NO: 14), compared to scrPIF-2$_{(13)}$ (SEQ ID NO: 8). The time dependent PIF-1 immunomodulatory effects are demonstrated in Table 3 below.

TABLE 3

Time-dependent immunomodulatory effects of PIF-1

| pg/ml | Hours Post Induction | PHA | Veh | DMSO CON | PIF | PIF-MabCD3 | PIF-scr | PIF-scr MABCD3 | CD3-C | PBS |
|---|---|---|---|---|---|---|---|---|---|---|
| TNF-α | 4 | 18829.1 | 0 | 0 | 0 | 481.6 | 0 | 1175.6 | 1189.4 | 0 |
|  | 24 | >11390 | 0 | 34.3 | 38.0 | >11390 | 5095.6 | 4058.1 | 0 | 0 |
|  | 48 | 0 | 554.1 | 1691.7 | 0 | >11390 | 4071.2 | 0 | 0 | 0 |
|  | 96 | 0 | 40.9 | 215.8 | 0 | 0 | 299.7 | 0 | 0 | 0 |
| IFN-γ | 4 | 0 | 0 | 0 | 0 | 0 | 0 | 0 | 0 | 0 |
|  | 24 | 1728.8 | 0 | 0 | 0 | 0 | 27.7 | 18.1 | 0 | 0 |
|  | 48 | 0 | 0 | 0 | 0 | >4740 | 124.3 | 0 | 0 | 0 |
|  | 96 | 0 | 0 | 0 | 0 | 0 | 16.2 | 0 | 0 | 0 |
| IL-1β | 4 | 891.2 | 0 | 0 | 0 | 0 | 0 | 20.3 | 20.7 | 0 |
|  | 24 | 5010.5 | 0 | 0 | 0 | 2914.1 | 85.7 | 75.0 | 0 | 0 |
|  | 48 | 0 | 44.4 | 58.0 | 0 | 3295.4 | 181.6 | 0 | 0 | 0 |
|  | 96 | 0 | 26.5 | 55.0 | 0 | 0 | 57.0 | 0 | 0 | 0 |
| IL-6 | 4 | 7045.0 | 0 | 0 | 0 | 17.5 | 0 | 20.3 | 21.3 | 0 |
|  | 24 | >5200 | 0 | 0 | 36.3 | >5200 | 65.5 | 46.7 | 0 | 0 |
|  | 48 | 0 | 34.6 | 43.9 | 0 | >5200 | 1061.0 | 16.3 | 0 | 0 |
|  | 96 | 0 | 27.5 | 67.7 | 0 | 0 | 55.3 | 0 | 0 | 0 |
| IL-2 | 4 | 28.7 | 0 | 0 | 0 | 0 | 0 | 0 | 0 | 0 |
|  | 24 | 2800.6 | 0 | 0 | 0 | 9045.7 | 35.8 | 33.7 | 0 | 0 |
|  | 48 | 0 | 0 | 0 | 0 | 6015.3 | 0 | 0 | 0 | 0 |
|  | 96 | 0 | 0 | 0 | 0 | 0 | 0 | 0 | 0 | 0 |
| IL-5 | 4 | 0 | 0 | 0 | 0 | 0 | 0 | 0 | 0 | 0 |
|  | 24 | 125.0 | 0 | 0 | 0 | 397.5 | 0 | 0 | 0 | 0 |
|  | 48 | 0 | 0 | 0 | 0 | 943.6 | 0 | 0 | 0 | 0 |
|  | 96 | 0 | 0 | 0 | 0 | 0 | 0 | 0 | 0 | 0 |
| IL-8 | 4 | 0 | 885.0 | 711.4 | 684.5 | 514.8 | 792.5 | 513.7 | 552.0 | 739.8 |
|  | 24 | >6330 | >6330 | 4559.3 | >6330 | >6330 | >6330 | >6330 | >6330 | 5440.5 |
|  | 48 | 5634.0 | >6330 | >6330 | >6330 | >6330 | >6330 | 7544.2 | 7488.7 | >6330 |
|  | 96 | >6330 | >6330 | >6330 | 6679.0 | 0 | >6330 | 0 | 0 | 0 |
| GM-CSF | 4 | 60.4 | 0 | 0 | 0 | 0 | 0 | 0 | 0 | 0 |
|  | 24 | 60.0 | 0 | 0 | 0 | 58.9 | 0 | 0 | 0 | 0 |
|  | 48 | 0 | 0 | 0 | 0 | 0 | 0 | 0 | 0 | 0 |
|  | 96 | 0 | 0 | 0 | 0 | 0 | 0 | 0 | 0 | 0 |
| IL-4 | 4 | 0 | 0 | 0 | 0 | 0 | 0 | 0 | 0 | 0 |
|  | 24 | 60.0 | 0 | 0 | 0 | 58.9 | 0 | 0 | 0 | 0 |
|  | 48 | 0 | 0 | 0 | 0 | 0 | 0 | 0 | 0 | 0 |
|  | 96 | 0 | 0 | 0 | 0 | 0 | 0 | 0 | 0 | 0 |
| IL-10 | 4 | 13.3 | 0 | 0 | 0 | 0 | 0 | 0 | 0 | 0 |
|  | 24 | 1411.5 | 0 | 0 | 0 | 1710.1 | 21.3 | 17.5 | 0 | 0 |
|  | 48 | 0 | 0 | 17.5 | 0 | 664.9 | 18.4 | 0 | 0 | 0 |
|  | 96 | 0 | 0 | 0 | 0 | 0 | 0 | 0 | 0 | 0 |

PHA - 20 μg/ml
Veh, vehicle control for PHA (=RPMI1640)
DMSO con, CON for PIF and PIFscr (0.005%/v/v DMSO)
MabCD3-C, coated wells (10 μg/ml in PBS overnight at 4° C. 50 uL per well)
PBS-C, PBS coated controls for MabCD3 (as MabCD3)

Detailed time dependent and multiple controls were used the secretion of several cytokines by PBMC (IL-2, IL-5, IL-8, GM-CSF, IL-4, IL-10, TNF-α, IFN-γβ, IL-1 and IL-6) were measured. Using CD3MAb as mitogen, PIF-1 stimulated mitogen-induced but not basal immune response in a time dependent manner most effects were noted at 24-48 hours. By 4 hours, sPIF-1 blocked TNF alpha with recovery by 24 hours. Also INFgamma secretion initiated only after 48 hours. Major increase in a $T_h2$ cytokine (IL10) after 24 hours.

scrPIF-1$_{15}$ (SEQ ID NO:5) had an early and consistent stimulatory effect only on TNFalpha. Effects on cytokines was already noted at 0.7 nM. Similar effects were found also with other mitogens LPS and PHA when PIF-1 was tested.

Table 4 shows the effect of PIF-1 vs MVRIK (SEQ ID NO: 18) portion of the molecule and PGSA (SEQ ID NO: 19) portion of the molecule on cytokine secretion following exposure to CD3Mab.

TABLE 4

PIF and analogues on release of cytokines +/− platebound mAbCD3

| Sample | IL-1β | IL-2 | IL-4 | IL-5 | IL-6 | IL-8 | IL-10 | GM-CSF | IFN-g | TNFa |
|---|---|---|---|---|---|---|---|---|---|---|
| C-PIF/50 | 4.4 | 31.0 | 17.9 | 0 | 287.7 | >5000 | 77.0 | 29.1 | 130.3 | 223.5 |
| C-PIF/1 | 3.4 | 21.4 | 17.2 | 0 | 204.2 | >5000 | 72.9 | 20.7 | 122.6 | 135.7 |
| C-scr/50 | 7.4 | 16.2 | 16.4 | 0 | 200.9 | >5000 | 66.7 | 19.3 | 104.7 | 115.6 |
| C-scr/1 | 3.8 | 20.5 | 17.8 | 0 | 176.8 | >5000 | 51.9 | 19.2 | 102.1 | 120.8 |

TABLE 4-continued

PIF and analogues on release of cytokines +/− platebound mAbCD3

| Sample | IL-1β | IL-2 | IL-4 | IL-5 | IL-6 | IL-8 | IL-10 | GM-CSM | IFN-g | TNFa |
|---|---|---|---|---|---|---|---|---|---|---|
| C-PIF-4/50 | 7.3 | 36.2 | 17.8 | 8.6 | 270.1 | >5000 | 82.5 | 27.3 | 145.4 | 299.9 |
| C-PIF-4/1 | 6.0 | 24.0 | 0 | 0 | 233.6 | >5000 | 44.1 | 13.7 | 81.3 | 68.3 |
| C-PIF-5/50 | 5.3 | 20.0 | 0 | 0 | 178.9 | >5000 | 57.2 | 20.7 | 81.2 | 81.1 |
| C-PIF-5/1 | 10.7 | 19.2 | 16.93 | 0 | 221.8 | >5000 | 68.5 | 26.8 | 98.2 | 142.8 |
| C-PIF-9/50 | 7.8 | 33.7 | 18.16 | 0 | 249.4 | >5000 | 105.0 | 25.3 | 132.1 | 160.8 |
| C-PIF-9/1 | 4.8 | 26.4 | 0 | 0 | 177.6 | >5000 | 49.0 | 14.3 | 86.5 | 60.1 |
| C-CD3 | 13.4 | 18.6 | 17.3 | 0 | 169.5 | >5000 | 43.5 | 13.4 | 75.6 | 50.5 |
| U-PIF/50 | 0 | 0 | 0 | 0 | 37.8 | 1426.7 | 0 | 0 | 0 | 0 |
| U-PIF/1 | 0 | 19.9 | 0 | 0 | 32.2 | 963.0 | 0 | 12.5 | 0 | 0 |
| U-scr/50 | 0 | 0 | 0 | 0 | 36.5 | 1071.6 | 0 | 0 | 0 | 0 |
| U-scr/1 | 0 | 0 | 0 | 0 | 39.6 | 1243.1 | 0 | 10.3 | 0 | 0 |
| U-PIF-4/50 | 0 | 0 | 0 | 0 | 33.4 | 1079.9 | 0 | 0 | 0 | 0 |
| U-PIF-4/1 | 0 | 0 | 0 | 0 | 32.9 | 809.3 | 0 | 0 | 0 | 0 |
| U-PIF-5/50 | 0 | 0 | 0 | 0 | 37.6 | 786.4 | 0 | 0 | 0 | 0 |
| U-PIF-5/1 | 0 | 0 | 0 | 0 | 28.9 | 763.6 | 0 | 0 | 0 | 0 |
| U-PIF-9/50 | 0 | 13.1 | 0 | 0 | 38.7 | 1480.2 | 0 | 0 | 0 | 0 |
| U-PIF-9/1 | 0 | 0 | 0 | 0 | 40.8 | 772.46 | 0 | 0 | 0 | 0 |
| U-Veh | 0 | 0 | 0 | 0 | 31.4 | 898.4 | 0 | 0 | 0 | 0 |

It appears that PGSA (C-PIF-4 in Table 4 above) (SEQ ID NO: 19) has a similar effect to the 9 amino acid sequence (C-PIF-9 in Table 4 above) with respect to several cytokines, the effect being dose dependent. The effect of MVRIK (SEQ ID NO: 18) was in comparison mild. In non-stimulated PBMC, the 9 amino acid PIF and the 4 amino acid PIF (SEQ ID NO: 19) had a stimulatory effect on IL6 and 8. This illustrates that from the 15 amino acid original nPIF-1, a synthetic derivative of 4 amino acids appears to contain a portion of the bioactivity on cytokine secretion.

The effect of PIF-1 was examined on THP1 a monocyte cell line (Dr Sharma Brown Univ). Exposure to 1-100 nM caused a dose dependent increase in IL10 secretion, further documenting that since monocytes have already have 99% of the PIF-1 receptors expressed under unstimulated condition the PIF does not require a mitogen to express the Th2 type cytokine.

PIF-1 Effect on Kinases

The effect of PIF-1 on kinases related to metabolic function was examined. The methodology for testing PIF activity on MEK1 kinase is described below, but it is applicable for all kinases tested: 50 nM Tris pH, 0.1 mM EGTA 0.10% b-mercaptoethanol 1 mg/mg BSA PIF-1 15 was dissolved in deionised water at 5 nM-5 uM range of concentrations. The final reaction of MEK-1 5-10 mU incubated with 8 mM MOPS pH 7.0 0.2 EDTA, 50 uM EAIYAAPFAKKK (SEQ ID NO: 23), 10 mM Mg Acetate and [gamma-33P-ATP] 500 cpm/pmol. Reaction initiated with addition of MgATP. After 40 minutes incubation at room temperature, reaction stopped by the addition of 5 ul of a 3% phosphoric acid solution. 10 ul of the reaction is spotted onto a P30 filtermat and washed three times for 5 min in 75 mM phosphoric acid and once in methanol prior to drying and scintillation counting.

The effects of PIF on 46 different kinases (listed below in Table 5) related to metabolic function were tested. The results indicate that PIF-1 does not interact with any of kinases (data not shown). Non-reactivity suggests that PIF effect is very specific and is exerted on the PBMC immunity, while not interfering with other metabolic functions, which would be viewed as toxicity. List of kinases (FASTKINASE) panel conducted at MDSPS, Bothell Wa (Dr David Kirk).

TABLE 5

Kinases tested

| ABL1 | FGFR3 | MEK1 | ROS |
| AKT1 | FGFR4 | c-MET | RSE |
| ARG | FGR | MSK1 | RSK2 |
| ECG | FLT3 | p38α | SGK1 |
| EPH1 | HCK | p38β | SRC |
| EPHB2 | HER2 | p38δ | SYK |
| EPHB3 | IRK | p38γ | TRKA |
| EPHB4 | JK1 | P70S6 | TRKB |
| ERK1 | JNK2 | PDGFα | YES |
| ERK2 | c-KIT | PDGFβ | ZAP70 |
| FES | LCK | PKA | |
| FGFR1 | LYNA | ROCK2 | |

PIF Correlates with an In-Vivo Pro-Inflammatory Response

PIF activity was measured in normal (n=4) and thrombophilic pregnancies (n=4) using a FC bioassay based upon CD2 binding to Jurkat leukemia cell line. A correlation between PIF activity and IL-1 in normal pregnancies was observed, but not in thrombophilic conditions (p=0.02). No correlation was observed between PIF and TNF α, IL-8 or thrombus precursor protein (TpP) in either normal pregnancies or thrombophilic conditions. Results appear to indicate that the embryo directs maternal immune response, rather than playing a passive role and that PIF may be an early indicator of pregnancy well-being.

Dynamics of Synthetic PIF-1 Interaction with Resting/Activated PBMC

Figure 3:
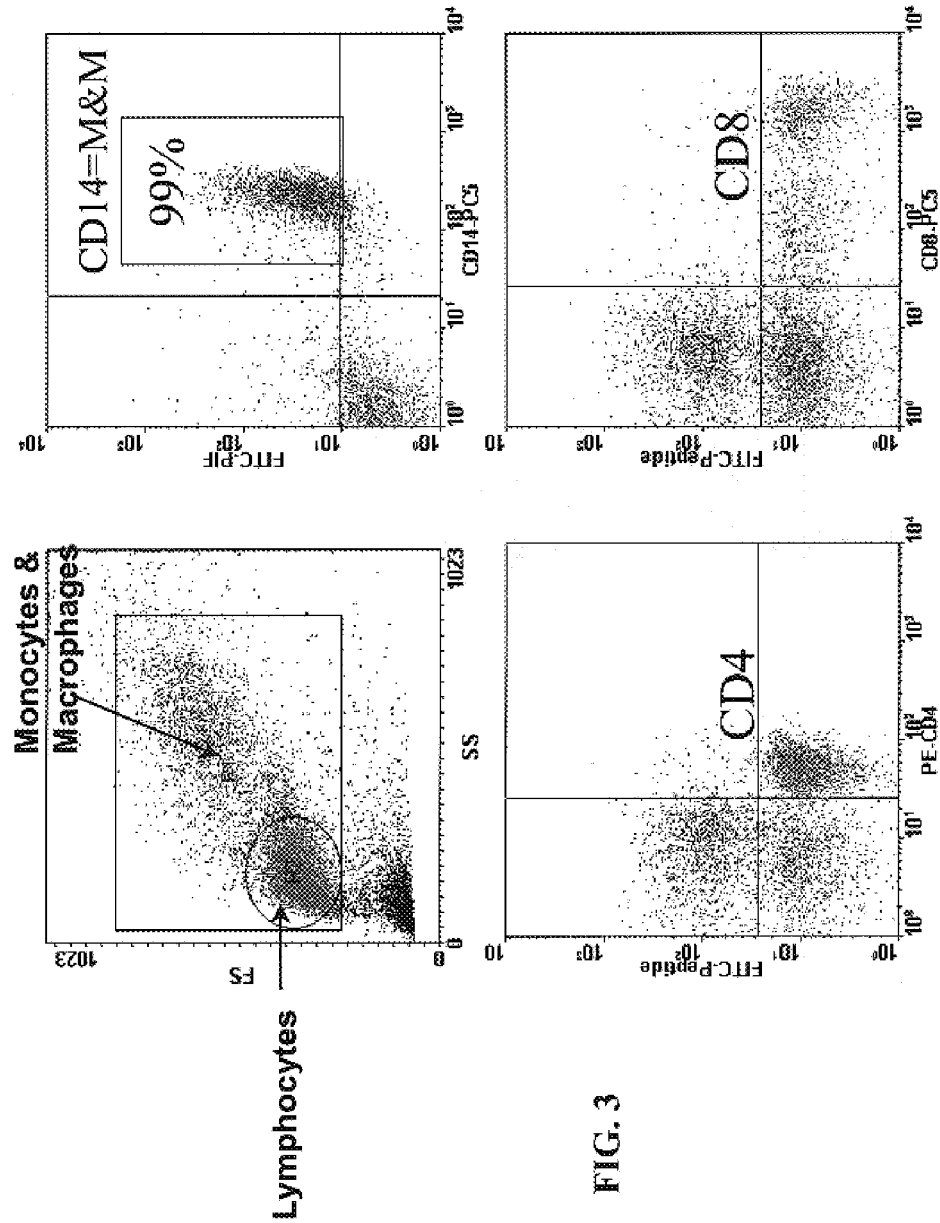
FIG. 3. shows preferential binding of FITC sPIF-1 (SEQ ID NO:13) to subpopulation of PBMC. sPIF-1 binds monocytes and macrophages (primary antigen presenting cells) at the basal state. FITC labeled PIF-1 was added to unstimulated PBMC. Binding of the labeled peptide to PBMC subpopulation was determined by using specific CD markers. CD14+ cells represents monocytes.

The expression of PIF binding sites was examined utilizing flow cytometry studies employing FITC labeled sPIF-1$_{15}$ (SEQ ID NO: 13) and PBMC from normal human donors showed that it binds to a small number of naive T cells. As shown in FIG. 3, sPIF-1$_{15}$ (SEQ ID NO: 13) binds to monocytes and macrophages, the primary antigen presenting cells, at basal state. In contrast, sPIF-1$_{15}$ (SEQ ID NO: 13) binds all monocytes but not to platelets. Without wishing to be bound by theory, this suggests that monocytes and a sub-set of T cells express prior to pregnancy receptors, and also indicates that although sPIF-1$_{15}$ (SEQ ID NO: 13) is somehow similar enough to CD2 that it binds to anti-CD2, it does not bind to the platelet marker CD58, as does CD2 itself. PIF-1 sequence has no homology to that of CD2.

Figure 4:
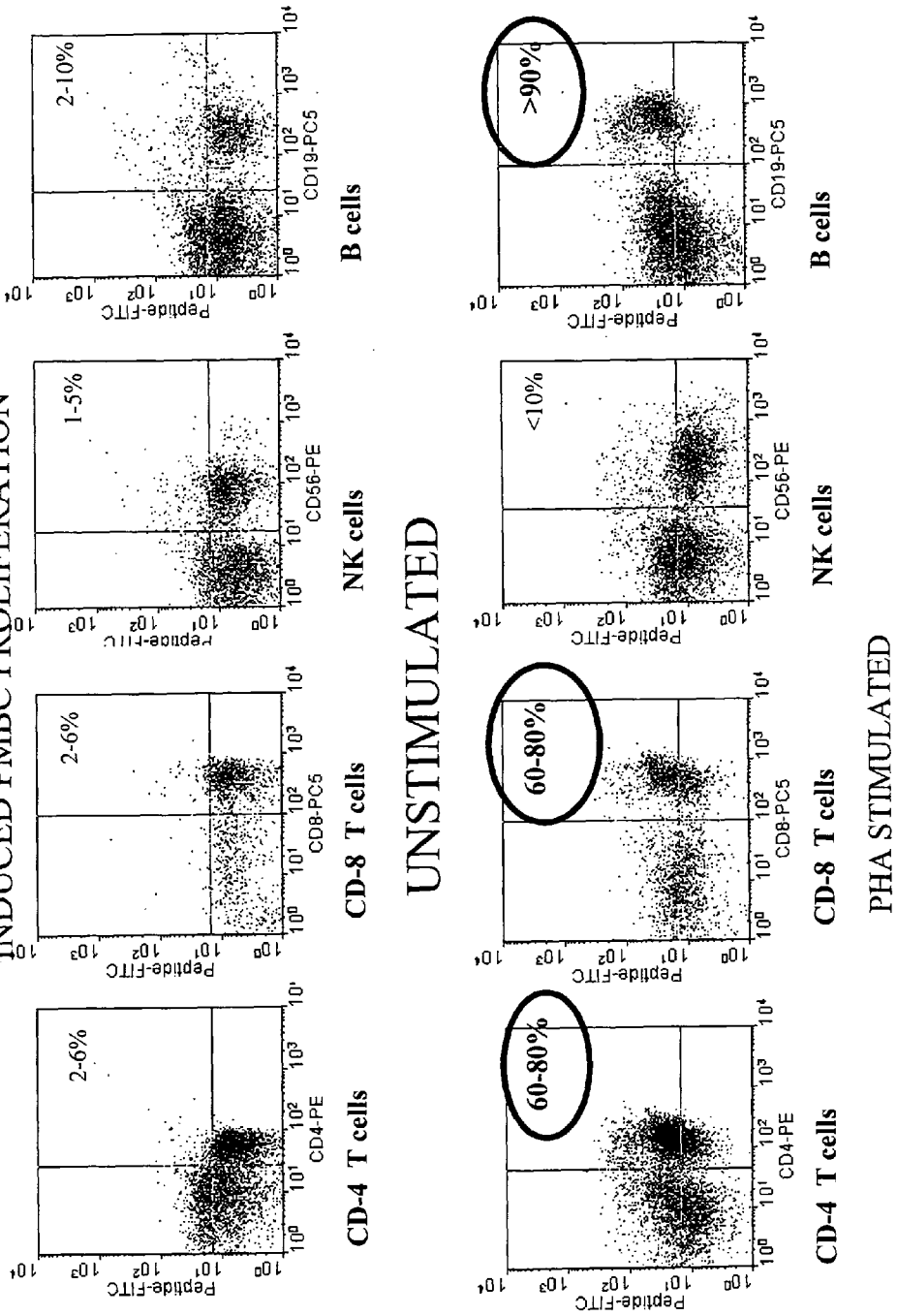
FIG. 4 shows effects of binding by FITC sPIF-$1_{(15)}$ (SEQ ID NO:13) to basal and PHA stimulated PBMC PIF receptors. Expression of PIF-$1_{(15)}$ (SEQ ID NO:1), receptor following PHA induced PBMC proliferation CD-4 T cells; CD-8 T cells; NK cell and B cells (unstimulated-top); (PHA stimulated-bottom). Flow cytometry analysis of PBMC following exposure to FITC sPIF-$1_{(15)}$ (SEQ ID NO:13) % expression was determined in PBMC subtypes before and after exposure to 1 ug/ml PHA for 24 hours. There was a major increase in PIF-1 (SEQ ID NO:1) receptors expression on T (CD4, CD8 cells, 60-80%) and B cells (>90%), while no changes in the NK cells receptors was noted. This indicates that both T cells (cellular immunity) and B cells (antigen presenting cells) increase PIF-1 receptor expression markedly within 24 hours. Macrophages/monocytes have already a full complement of PIF receptors (first responders). In contrast, minimal receptors expression could be induced by the mitogen on NK (natural killer) cells that are supposed to be protect the body's basal immune response. The delay seen by PIF effects on mitogen induced PBMC cytokines secretion (24 h following exposure) may be explained by requirement for receptor induction (takes 24 hours). Therefore, an only 4 hours exposure had no effect (see Table 1).

Using flow cytometry fluoroscein-labeled sPIF-1$_{15}$ (SEQ ID NO: 13) binding to immune cells was examined on resting PBMC. Monocytes (CD 14+ cells) express binding sites on most cells, while the expression on resting T cells (CD4+ and CD8+), B cells (CD 19+) or NK cells (CD56) populations remained very low. As shown in FIG. 4, within 24 hrs of activation by PBMC cultured with the T-cell mitogen, phytohemmaglutinin (PHA)), 60-80% of T lymphocytes (T helper cells, T cytotoxic cells), and >90% of B cells became positive for the fluorescent sPIF-1$_{15}$ (SEQ ID NO: 13) binding, demonstrating that lymphocytes can recognize preimplantation factors and may respond to them but only if activated. NK cells did not appear to bind sPIF-1$_{15}$ (SEQ ID NO: 13) even after several days in culture with PHA.

PIF Likely Acts Through an Inducible Unique Immune Cell Surface Receptors

Fluorescent PIF peptides bind to immune cell membranes following activation. In order to better evaluate the receptor site that is an activation marker, flow cytometry (FC) using specific CD marker antibodies was performed. CD69 is expressed during activation of lymphocytes and monocytes, and is a marker of NK cells activation. CD25 is the receptor for IL-2, and a known activation marker as well. The size of these molecules' positive cell population did not correlate with the sPIF-1$_{15}$ (SEQ ID NO:13) positive populations. The expression of CD3 in PBMC was examined following exposure for 3 days to sPIF-1$_{(15)}$ (SEQ ID NO:13) (2-200 nM) using 20 ul MAbCD3-PE (BD). There was between about 215-420% increase in the receptor expression. Exposure to PIF-2 caused a lesser increased of about 180-230% when examined with flow cytometry. There was also an increase in CD2 expression following the same type experiment used as above, but using CD2MAb-FITC. With PIF-1, the increase was between about 170-200% and with PIF-2, the increase was between about 125-160%. This confirmed that PIF receptors in the immune system are unique and selectively expressed on subpopulation of immune cells and they are inducible by mitogenic activation. scrPIF-1$_{(15)}$ (SEQ ID NO:5) inhibitory action appears to be exerted on the PIF binding site.

Figure 13:
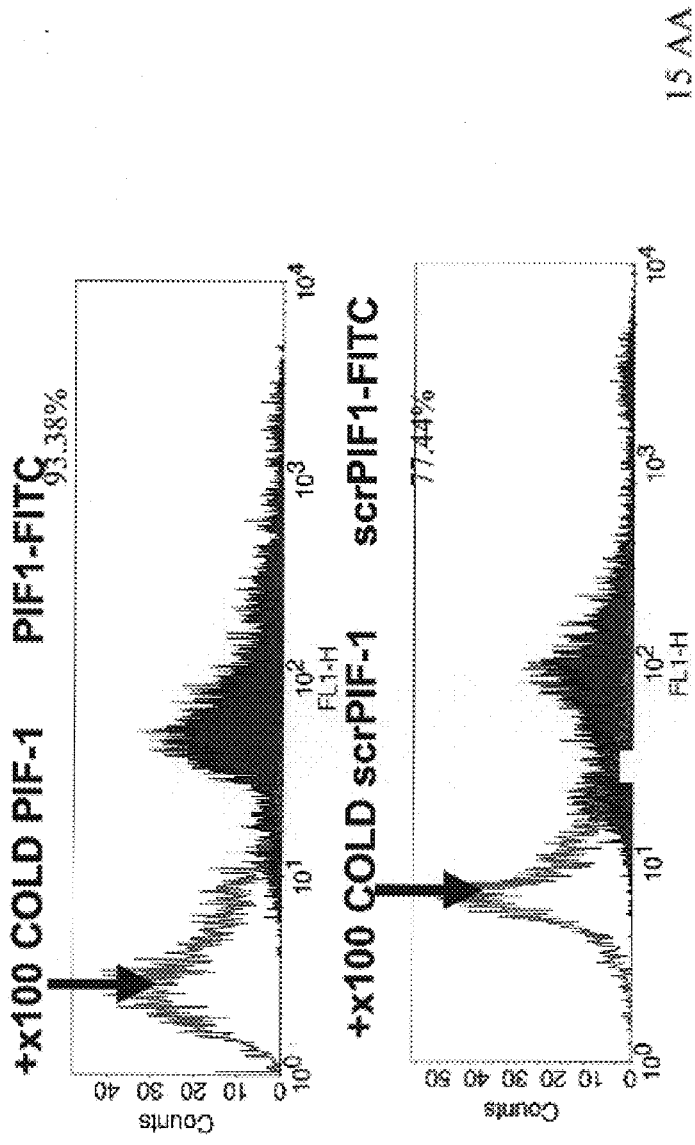
FIG. 13 reflects PIF-1 binding to mouse splenocytes. Virgin female C57Bl/6 mice were sacrificed and spleen cells were isolated and placed in AIM V culture media with 300 nM FITC PIF-1 (15)+/−100 fold excess unlabeled PIF. Following incubation cells were placed in a flow cytometry and the percentage of cells stained examined. Upper panel shows that addition of the unlabeled peptide led to >90% dissociation of FITC PIF from the PIF receptor. This confirms the in vivo mouse experiments where the injected FITC principally accumulated in the spleen). Lower panel shows the same experiment but with scrPIF-1. Here specific binding to the PIF receptor was noted but at a lower affinity. This is in accord with the cytokine data (see below).

FIG. 13 shows how sPIF-1$_{(15)}$ (SEQ ID NO: 13) and scrPIF-1 (SEQ ID NO:5) bind specifically to immune cells. Splenocytes from virgin female C57BL/6 mice were stained with 300 nM of PIF-1-FITC or scrPIF-1-FITC. Filled histograms indicated PIF-1-FITC or scrPIF-1-FITC alone. Empty histograms represent PIF-1-FITC or scrPIF-1-FITC staining in the presence of 100-fold excess of corresponding unlabeled peptide. Histograms represent both monocytes and lymphocytes according to scatter gating. These results show that fluorescent-labeled sPIF-1$_{(15)}$ (SEQ ID NO: 13) and scrPIF-1 (SEQ ID NO:5) binding is competed out by unlabeled PIF and scrPIF. scrPIF binding is specific, however, the immune effect is negated (see above).

In addition, isolated splenocytes were stimulated with PMA 50 ng/ml/Ionomycin 500 ng/ml, LPS or PHA with overnight +/−sPIF-1$_{(15)}$ (SEQ ID NO: 13) 300-3000 nM+/−10 fold unlabeled peptide. Compared to unstimulated cells, the profile of scatter of binding displacement was different between sPIF-1$_{(15)}$ (SEQ ID NO: 13) and scrPIF-1 (SEQ ID NO:5) under all stimulations. This indicates that splenocytes response to PIF-1 differs based on the stimulus given. There were also are significant differences with cell properties when the PIF-1 is utilized in contrast to use of scrPIF.

While not wishing to be bound by theory, it is believed that PIF acts on PBMC through calcineurin, NFAT pathways. PIF-1 appears to attach to specific high affinity binding sites, at the nM range. We have examined using calcium mobilization in T cells which is central to T-Cell activation initiated by antigen presentation to the T-Cell Receptor (TCR) antigen whether PIF-1 acts through mobilization of Ca++flux. Activation of T-cells was carried out by using phorbal ester (PMA) and Ca2+ ionomycin both of which synergize through two different signaling pathways the former through Protein Kinase C, while the later through Tyrosine Kinases. In both cases, PIF-1 at 1 nM-50 uM concentration did not affect Ca++mobilization. We have also looked at Tcell activation using PHA. PHA stimulation of Ca2+ influx is not as marked as Ionomycin/PMA, but it is measurable and again PIF does not show any inhibition. This tends to confirm, using a different mitogen, that PIF acts downstream of the Ca++ step. Interestingly, the ionomycin pathway, after Ca++ mobilization, signals by calmodulin through calcineurin which is inhibited by cyclosporin A (CsA) and FK506, which are the two major agents used currently to promote organ transplants tolerance, PIF-1 action may involve such a pathway. This also strongly suggests that PIF-1 action does not involve binding to the G-protein coupled receptors signal, since most involve Ca++ action.

Calcium channel analysis method: 2E6 freshly isolated PBMC in RPMI1640+10% FBS (HI) and equilibrated for 24 hours. Cells are loaded with a proprietary dye that fluorescence when bound with Ca++. PIF-11 or 50 nM as well as 1-50 nM scrPIF-1 were added prior to inducing the cells with PMA/ionomycin or PHA 20 ug/ml or vehicle 0.005% DMSO. PIF-1 treated cells are loaded into the Flexstation and the inducer is added robotically with a liquid handler. At a precise time fluorescence monitoring commences. CA++ mobilization involves initially at least sequestered within organelles to the cytoplasm where it binds with the dye and produces a fluorescent signal.

PIF-1 Enhances Endometrial Receptivity

Human endometrial tissues were digested and stromal and epithelial cells (hEEC) isolated and cultured with a fetal bovine serum (FBS)-enriched medium until confluent layers were obtained. After that the cells were cultured for two more days in a FBS free-medium followed by a further 2-day culture in the same medium containing PIF peptides (1-500 nM). The expression of β-3 integrin by hEEC was qualitatively determined by immunocytochemistry and quantitatively measured by flow cytometry using a specific anti-β-3 integrin monoclonal antibody (SS A6). sPIF-1$_{15}$ (SEQ ID NO:13) and sPIF-1$_{(9)}$ (SEQ ID NO: 16) isoforms and sPIF-2$_{(13)}$ (SEQ ID NO: 8) treatment of hEEC exhibits up to a four-fold increase in the expression of β-3-epithelial integrin. This data indicates that preimplantion factor peptides released by the preimplantation embryo up-regulate the expression of an important marker for endometrial receptivity facilitating pregnancy initiation and maintenance.

In addition, to compare the recovery of β-3 integrin expression with PIF effects described after cultured hEEC in a free-fetal bovine serum (FBS) medium some cells were cultured again in FBS-medium. Interestingly, these cells expressed higher levels of β-3-integrin than did cells growing in free FBS-medium but still levels of β-3-integrin expression triggered by PIF effects were higher, as documented by both immunocytochemistry and flow cytometry. The effect of sPIF-1$_{(15)}$ (SEQ ID NO: 13) 10 nM was specific since it was blocked with scrPIF-1 (SEQ ID NO: 5) scrPIF-1 at 6.25 uM, by about 70%. Similar enhancement of beta integrin was achieved with PIF-1$_{(9)}$. In contrast, PIF did not interact with cultures of human endometrial stromal cells. These results could imply that PIF effects on β-3-integrin expression, which indicate an increase of endometrial receptivity, are higher that those triggered by a medium containing progesterone and an undefined variety and concentration of growth factors and hormones. PIF binding to epithelial cells was also examined. Binding was examined using MaBCD2 staining. Compared to non-relevant IgG, sPIF-1$_{(9)}$ (SEQ ID NO:16) and sPIF-1$_{(15)}$ (SEQ ID NO:13) had the highest binding, vs PIF-3 and PIF-2 which binding was only mild. showed that PIF binds to specific sites on epithelial cells.

sPIF-1$_{(15)}$ Identifies Abnormal Immune Response of a Patient with Recurrent Pregnancy Loss sPIF-1$_{15}$ (SEQ ID NO:13) effect was tested on a patient with over 14 miscarriages and no live birth. Her immune cells were examined in the non-pregnant state, by exposure to sPIF-1$_{15}$ (SEQ ID NO:13) using PBMC preparations. Induction of PIF receptor expression, and binding to lymphocytes were used to characterize the treated cells. Table 6 illustrates the ability of PIF assay to predict premature labor.

TABLE 6

Premature labor prediction using PIF-1

| Specimen | PHA | (PIF+/CD4+)/CD4+ | (PIF+/CD8+)/CD8+ | (PIF+/CD19+)/CD19+ |
|---|---|---|---|---|
| Control | + | 22.1 (0%) | 24.5 | 46.2 |
| Patient | + | 16.2 (−27%) | 16.3 (−33%) | 48.2 |

The patient's PIF receptors appear to be inducible by PHA as are those of the control subject. No differences were observed on B cells, but patient's T cells PIF receptor were ~30% less than the control. Table 7 shows ability of PIF assay to correlate with proinflammatory cytokines in coagulation disorder associated with pregnancy (thrombophylia).

TABLE 7

PIF-1 Effects on Cytokine Expression

| Specimen | PHA | PIF-1$_{15}$ | TNFα* | IL-10* | T$_H$1/T$_H$2 |
|---|---|---|---|---|---|
| patient | − | − | 7.98 | 7.77 | 1.03 |
| patient | + | − | 14.23 | 24.76 | 0.57 |
| patient | + | + | 18.32 | 24.32 | 0.75 (+32%) |
| control | − | − | 4.76 | 4.71 | 0.99 |
| control | + | − | 17.43 | 25.72 | 0.68 |
| control | + | + | 15.46 | 28.18 | 0.55 (−19%) |

*All cytokine numbers are % of total PBMC in scatter gate (including CD14) and 4 in table (above).

Under sPIF-1$_{(15)}$ (SEQ ID NO:13) influence, the T$_H$1/T$_H$2 ratio decreases (as expected) in the control specimen; but the same did not decrease in the patient's PBMC culture media (see bold numbers in table above).

The results obtained with this illustrative clinical case indicate that changes in the immune system of patients with poor obstetric history can be identified prior pregnancy by using PIFs as an embryo surrogate. Such testing can allow for pre-pregnancy identification of patients with poor ability to mount an immune change or tolerance to initiate and maintain pregnancy. Such an insight could help in screening patients at risk of miscarriage and lead to correction of the underlying pathologic condition perhaps by PIF administration. Such testing can be applied during pregnancy as well. Moreover, adding PIF to test the patient's endometrial cells properties (beta integrin or such), following collection by biopsy may help to determine whether the mother is able to respond to the presence of the embryo by increased receptivity.

Generate Polyclonal Antibodies to the Synthetic PIF-1, PIF-2 and PIF-3 Peptides To generate specific antibodies against sPIF-1$_{15}$ (SEQ ID NO:13) conjugation to carrier, Keyhole Limpet hemocyanin (KLH) was carried out. sPIF-1$_{15}$ (SEQ ID NO:13) was conjugated to KLH either on the carboxy or amine terminus of the molecule to cover potential differences in immunogenicity related to peptide presentation. The two peptide-carrier conjugates generated were injected into two rabbits. Within a 5-week immunization protocol all 4 rabbits responded by generating a high titer serum, with a titer of 1:50,000-1:150,000. The titer strength appeared to increase with the second bleeding. These rabbits may serve as a long-term reservoir of serum for antibody generation AbPIF-1$_{(15)}$. The rabbits may continue to be injected with immunogens on a monthly basis, collecting sera periodically and testing for titer and affinity. Antibodies to other PIFs, including AbPIF-2$_{(13)}$ and AbPIF-3$_{(18)}$, were generated with the same method using KLH bound peptide in the amine terminal. Rabbits bled 8 weeks after immunization yielded 1:25,000 titers for both peptides with detection of the PIF peptides to the nanomolar region. These antibodies were affinity purified using PIF-1, PIF-2 and PIF-3 bound affinity columns. The purified antibodies were conjugated each to a separate affinity column and they will serve for isolation of PIF peptides from various biological fluids.

Monoclonal antibodies to PIF-1 were developed as well. A hybridoma cell that produces a monoclonal antibody specific for a PIF polypeptide, and culturing the cell under conditions that permit production of the monoclonal antibody. ELISA results as standard curve and as comparison of PIF-1 spiked in FCS and monitoring antibody specificity with SELDI type mass spectrometry showed similar efficacy for a standard PIF-1 concentration.

Such PIF antibodies may be used in assay as well as in therapeutic treatment (vaccination) of patients. For example, PIF peptide conjugates may be used as antigen (vaccine) to fight malaria. PIF itself, being a minimal unit might behave as a better antigen than the when its sequence is embedded in the intact, full length circumsporozoite protein in the malaria outer cell membrane. In another example, PIF antagonist (a peptide or other chemical shown to bind to PIF receptors, and block PIF function) or any procedure whereby such compound is used as drug, may be useful to treat malaria or block malaria propagation in the human body (by blocking the sites through/by which the parasite controls and paralyses the immune system and allows it to proliferate). Similarly, any humanized or horse antibodies to PIF or a procedure whereby these are used as agents may be used for passive immunization for malaria. (assuming such antibodies must recognize the circumsporozoite protein on the malaria parasite).

In one example, polyclonal antibodies AbPIF-1$_{(15)}$ were generated against sPIF-1$_{(15)}$ (SEQ ID NO: 13) in rabbits (Covance Inc.). High titers 50% at 1:50,000 were achieved. Serial dilutions of synthetic sPIF-1$_{(15)}$ (SEQ ID NO: 13) were plated, blocked and then washed off. PIF-1 antibody (1:5000) was added incubated and washed off. Goat anti-rabbit antibody was added, incubated and washed off. Reaction was stopped by SDS and counted in plate reader (Biosynthesis Inc, G Vandydriff). As shown in the ELISA standard curve of FIG. 5A, PIF antibody detects low sPIF levels (pg). The antibody affinity was also confirmed by using a competition analysis between biotin labeled and unlabeled nPIF-1$_{(15)}$ (SEQ ID NO: 1) (data not shown). Also when scrPIF-1 (SEQ ID NO 5) was tested in the assay the antibody did not recognize it attesting to the high specificity of the antibody that was generated.

Figure 5B:
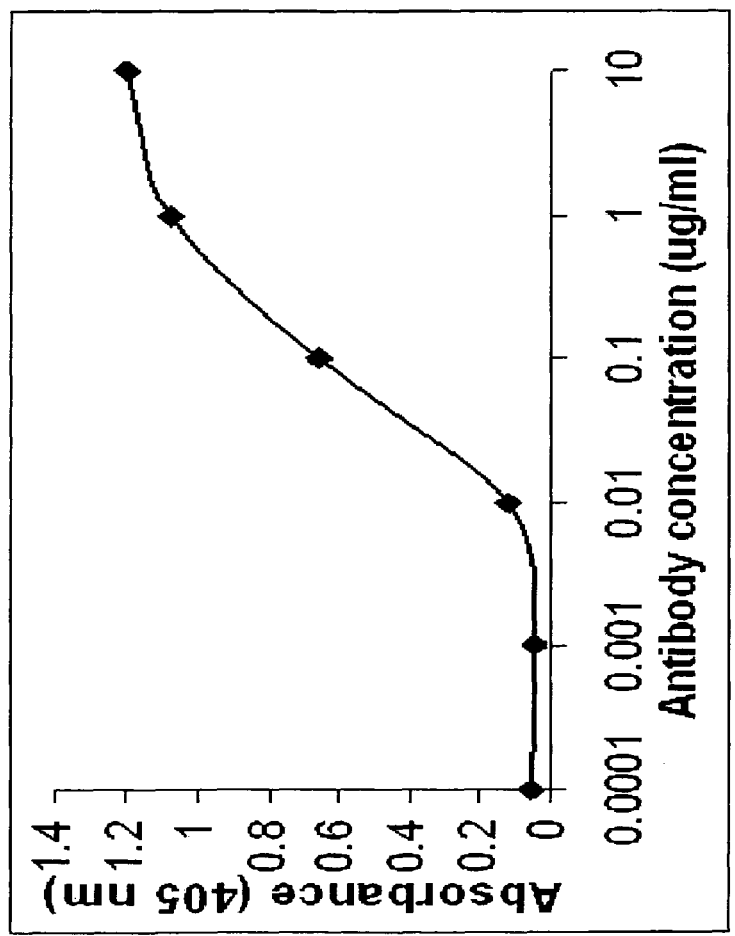
FIG. 5B shows ELISA profile of high affinity PIF-1 IgY antibodies (sandwich assay). Chickens were injected with KLH bound PIF-1 and the eggs were collected and affinity purified on a PIF column.

FIG. 5B demonstrates the affinity of PIF-1 IgY antibodies. Peptide as test antigen. Affi-pure IgY as the primary antibody and goat anti-Ig-Y as the secondary antibody. A fixed amount of antigen (5 ug/ml) and serial dilution of IgY.

Figure 6:
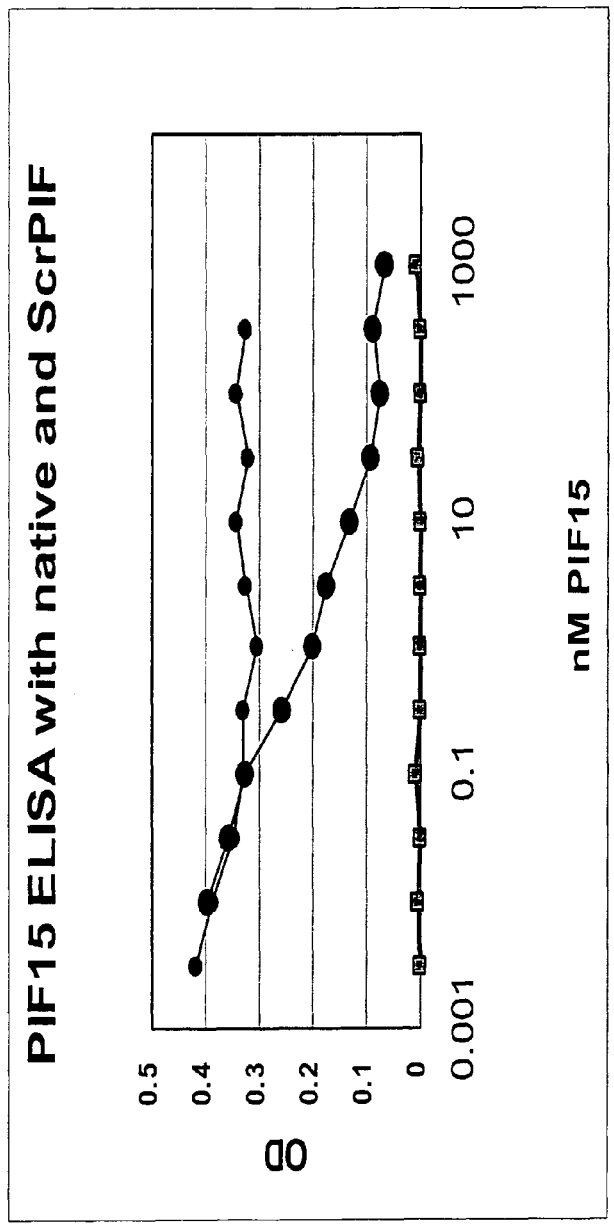
FIG. 6 shows ELISA profile of nPIF-$1_{(15)}$ and scrPIF-$1_{(15)}$ using Biotin labeled versus unlabeled peptide where the antibody captures the peptide in the unknown samples and compares it to standards.

FIG. 6 demonstrates the specificity of PIF-1 polyclonal antibody. At 4.5 ug/ml pAb coating concentration, PIF-1$_{15}$ was detectable at 10-30 μM in a dose response curve with an IC$_{50}$ of 500-700 pm, and linearly up to 30 nM. scrPIF-1 did not compete with biotinylated peptide, as the native. No binding appears to occur on uncoated plates, yielding a good background. Results demonstrate that PIF-1 polyclonal antibody appears to avoid false positives and negatives.

As shown in FIG. 20, PIF-1 monoclonal Ab which was generated in mice where the ELISA generated using 5 ug of PIF-1 was detected linearly with 10 ng/ml of the MAb.

Figure 16:
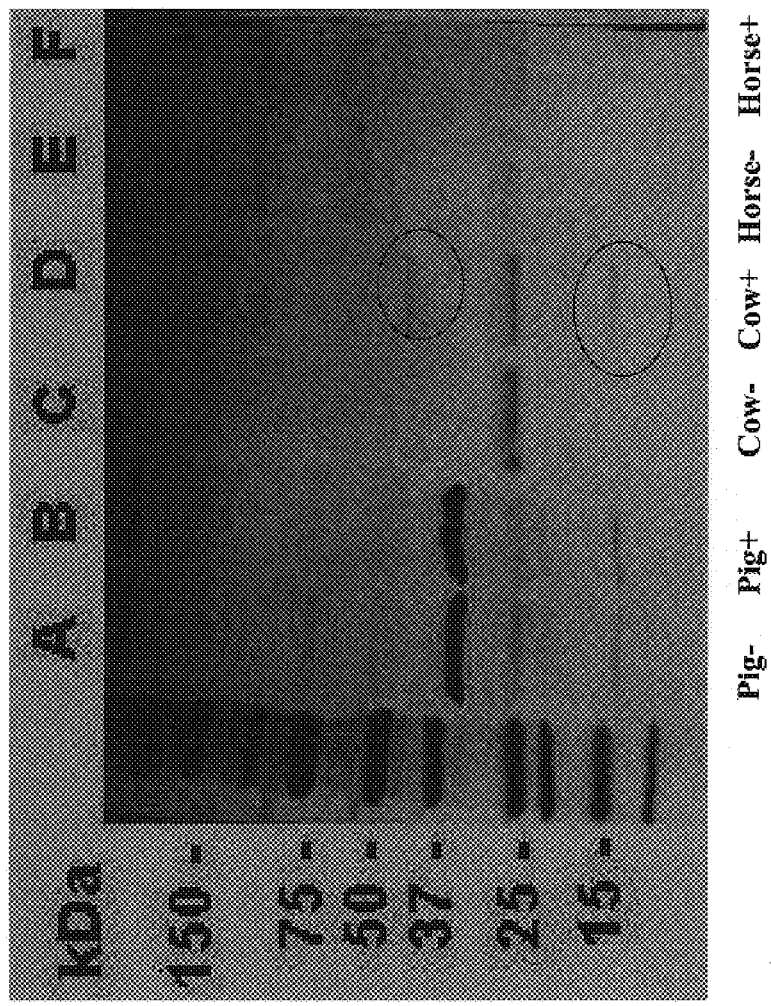
FIG. 16. Using affinity purified IgG, Western blot of serum showing differences in pregnant vs non pregnant cow, sow and horse serum.

Further, when fixed amount of PIF-1 was spiked into BS and the two antibodies were compared with a SELDI system their affinity was high and similar (FIG. 16). Using the SELDI method human embryo culture media were processed. Human embryo culture media samples were collected from viable embryos (Dr. Coulam, Chicago) and filtered through a 30 kDa filter using 70% ispropanol. Samples were placed on SELDI system microchambers, which were coated overnight with PIF-1 IgG antibody. Samples were compared to blank samples and MW of the peaks obtained was analyzed. The MW of PIF was compared with the embryo culture media sample. In contrast to media alone, several samples had PIF as estimated by mass spectrometry analysis. Such type of assessment may be used for determining which embryos should be transferred after IVF.

PIF Isolation and Identification in Embryo Culture Media

Figure 14A:
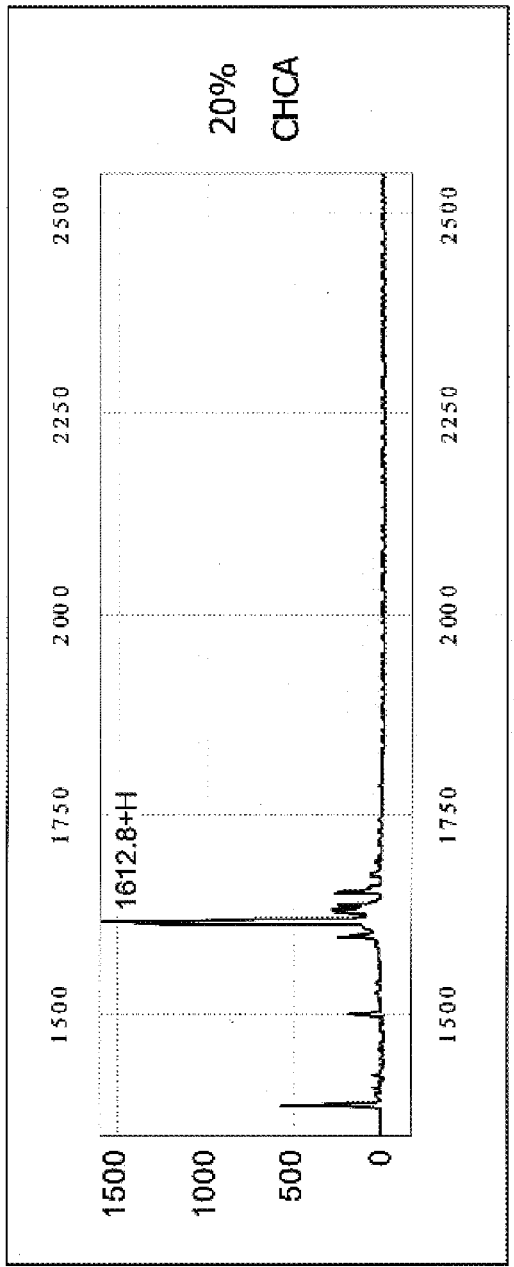
FIGS. 14A, B and C. (A, B) Show use of PIF-1 antibodies for detection of PIF-1 in solvent and FBS using the SELDI mass spectrometry method (Ciphergen inc, Amanda Bulman). Both the IgG and MAb detected the spiked PIF-1. Testing PIF-1 IgG and Mab. Validation for Abs specificity using Mass spec SELDI system. Demonstration of detection of PIF-1 in human embryo culture media (IVF) using IgG vs control media. (C) shows that PIF-1 can be detected by SELDI system using the IgG antibody.

In the present example, PIF was isolated and identified in human embryo culture media. sPIF-1 was added to 20% CHCA solution and was placed on SELDI (surface enhanced laser desorption/ionization) RS100 array. Sample was removed by pipet and the arrays were washed with 50 ml each the following sequence of buffers: (i) 1×PBS (5 min); (ii) 1× Urea IDM wash buffer (5 min); (ii) 1×PBS (5 min); (iii) 2×0.1% OGP (5 min); (iv) 2×PBS (5 min). 2×0.5 μl 10% saturated CHCA was added to each spot and collect data using SELDI system Protein chip system 4000 determining molecular weight by using mass spectrometry. As shown in FIG. 14A, the presence of PIF-1 at 1614 Da is shown.

Figure 14B:
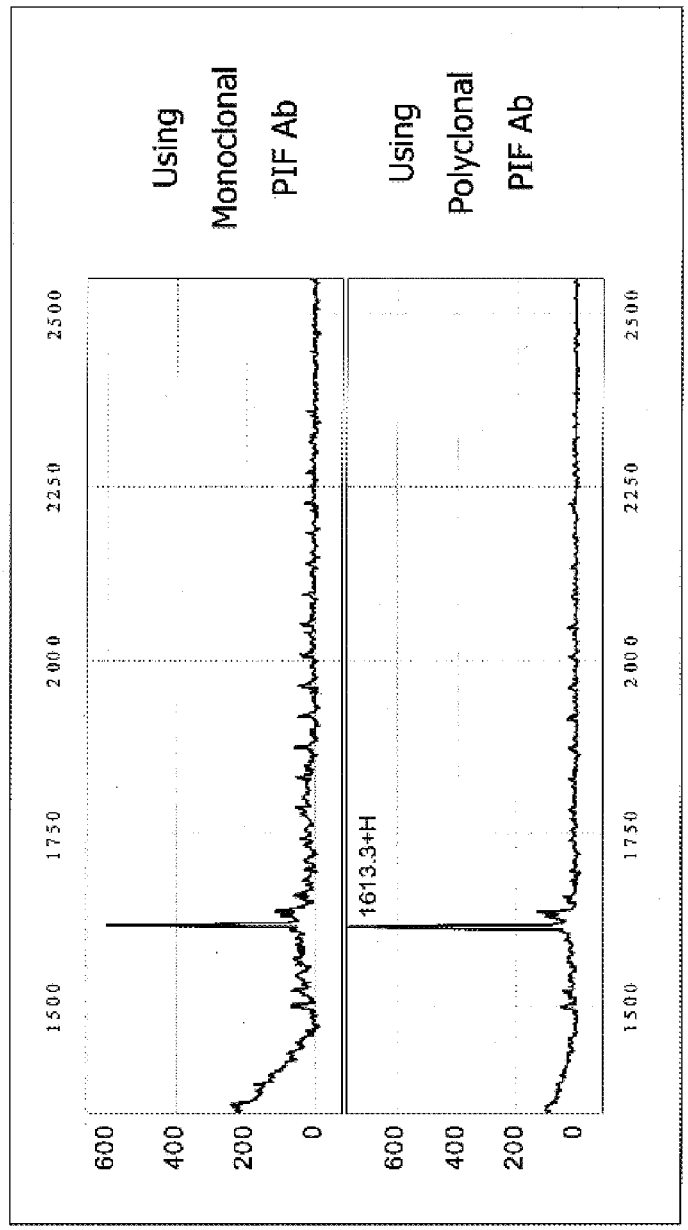

In a bioprocessor, spot 20 ml azide-free mouse monoclonal mouse PIF-1 antibody (0.05 mg/ml in PBS) or affinity purified IgG to preactivated RS100 arrays, incubating overnight at 4 C with gentle shaking. Add 20 μl blocking reagent (2 mg/mL BSA in PBS) to all spots and incubated for 1 hour at room temperature with gentle shaking. In the bioprocessor, wash each spot with 50 ml of PBS for 5 min and gentle shaking. Repeat. Incubate at room temperature 2 hours with gentle shaking. Add PIF-1 spiked in FBS. Remove each sample by pipet. Wash the arrays with 50 ml each the following sequence of buffers: (i) 1×PBS (5 min); (ii) 1× Urea IDM wash buffer (5 min); (iii) 1×PBS (5 min); (iv) 2×0.1% OGP (5 min); (v) 2×PBS (5 min). Add 2×0.5 μl 10% saturated CHCA to each spot and collect data using SELDI system Protein chip system determining MW by using mass spectrometry. As shown in FIG. 14B, PIF-1 presence was detected in human embryo culture media compared to media alone using both monoclonal and polyclonal antibodies.

In a bioprocessor, spot 20 ml azide-free mouse monoclonal mouse PIF-1 antibody (0.05 mg/ml in PBS) or affinity purified IgG to preactivated RS100 arrays, incubating overnight at 4 C with gentle shaking. Add 20 μl blocking reagent (2 mg/mL BSA in PBS) to all spots and incubated for 1 hour at room temperature with gentle shaking. In the bioprocessor, wash each spot with 50 ml of PBS for 5 min and gentle shaking. Repeat. Incubate at room temperature 2 hours with gentle shaking. Add samples (5 ul embryo culture media or media alone diluted in 1/10 70% isopropanol). Remove each sample by pipet. Wash the arrays with 50 ml each the following sequence of buffers: (i) 1×PBS (5 min); (ii) 1× Urea IDM wash buffer (5 min); (iii) 1×PBS (5 min); (iv) 2×0.1% OGP (5 min); (v) 2×PBS (5 min). Add 2×0.5 μl 10% saturated CHCA to each spot and collect data using SELDI system determining MW by using mass spectrometry determining presence of PIF-1 at 1614 in embryo culture media compared to media alone sample. FIG. 14C shows that PIF-1 can be detected by SELDI system using the IgG antibody. Compared to blank embryo culture media PIF-1 (15 aa size) was detected in several embryo culture media, while it was absent in 2 upper samples.

Isolation and Identification of PIF Like Proteins in Human Placenta and Other Fetal Tissues Using affinity purified PIF IgG 1, 2 and 3 and Igy PIF-1, PIFs were identified in human term placenta using Western blot. Western blots were prepared from Human Placenta Protein Medley (BD Biosciences, Catalog #: 7806-1, Lot #: 3100481, Source: Normal term and first trimester placenta. 10 mg/ml protein solution was provided in Laemmli sample buffer, 5% of β-mercaptoethanol was added to the samples, samples were boiled at 95° C. for 5 min, spun for 10 min. 50 ug and 100 ug of protein were loaded onto a 4-20% gradient SDS-polyacrylamide gel. The separated proteins were electrotransferred to PVDF membrane and, after 1 h blocking [Phosphate-buffer saline Dulbecco's, IX; 138 mM NaCl, 1.2 mM KH$_2$PO$_4$, 2.7 mM KCl, 8.1 mM Na$_2$HPO$_4$ (PBS)+5% dry milk], the membrane was incubated for 1 h at room temperature with a 1/50 dilution of the anti-PIF-1 polyclonal affinity purified chicken IgY (GenWay, Catalog #: A22922, Lot #: 04GA0005-040318, concentration: 1 mg/ml) or a 1/200 dilution of the anti-PIF-1 polyclonal Rabbit IgG in 5% milk-PBS or PIF-IMab 1/50. Following three washes 5 minutes each in PBS, the membrane was incubated with a 1/1000 dilution of horseradish peroxidase (HRP)-conjugated Goat anti-Chicken IgY Fc fragment (GenWay, Catalog #GAYFC-HRP) or HRP-conjugated Goat anti-Rabbit IgG (Pierce, N31460, Lot BA623816) for 1 h in 0.5% milk-PBS. Following three washes 5 minutes each in PBS, the final detection was performed using Opti-4CN Substrate Kit (Bio-Rad, Catalog #: 170-8235) according to manufacturer's protocol.

Figure 7:
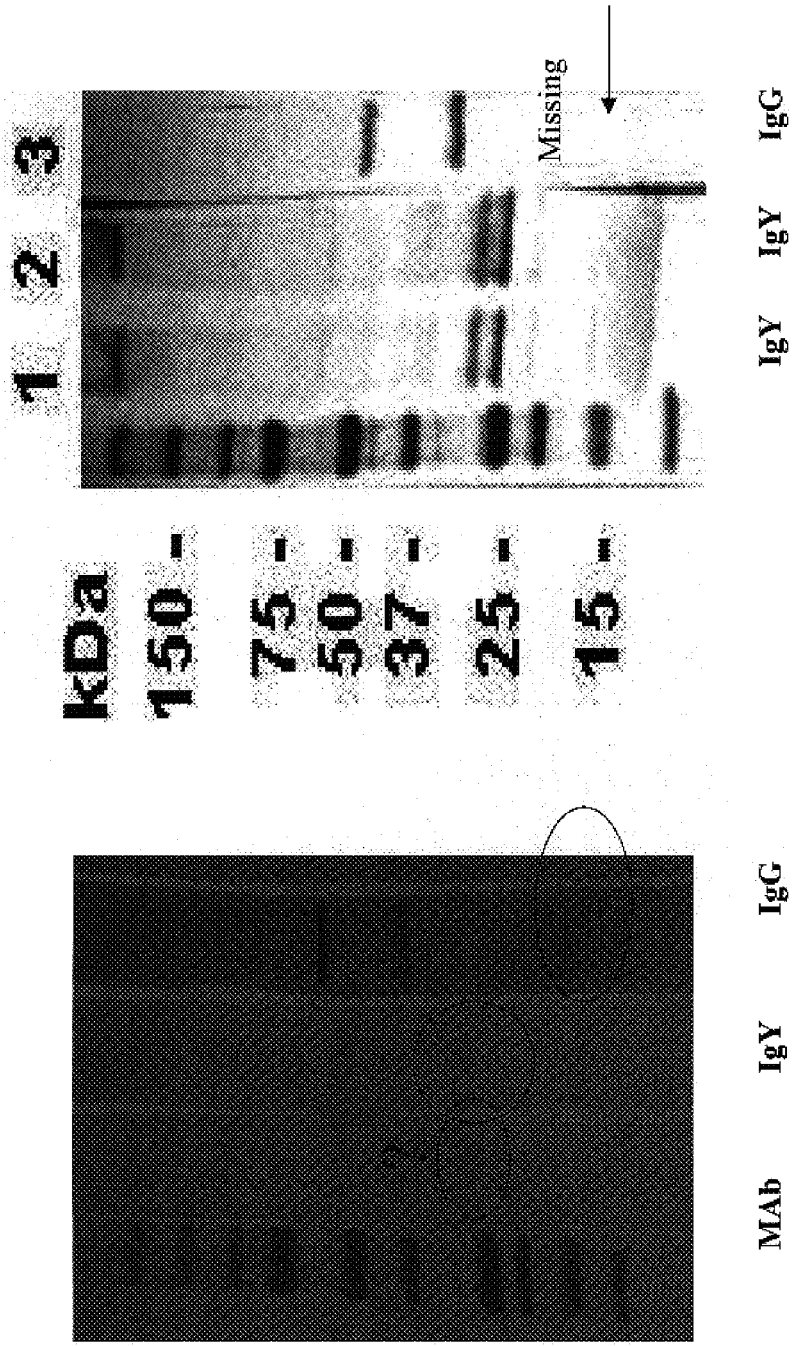
FIGS. 7 and 8. Human first trimester and term placental extracts were prepared (Dr Jerry Feitelson, GenWay, Inc) and were exposed to PIF-1, PIF-2 and PIF-3 antibodies using Western blot analysis. PIF like molecules were stained and the bands obtained were compared to a serial molecular weight standards run in parallel. Results showed that a number of PIF-1 related proteins are present at the 15-40 kDa range. PIF-3 had a lower intensity with and was associated with different molecular weight bands. Finally, PIF-2 expression was minimal. This supports the notion that the human placenta may have precursor proteins from which by cleavage PIF peptides are produced. This also supports that view that PIF like molecules are present throughout pregnancy. Finally, it documents that in terms of intensity of expression in human by far PIF-1 is the most relevant at term.
Figure 8:
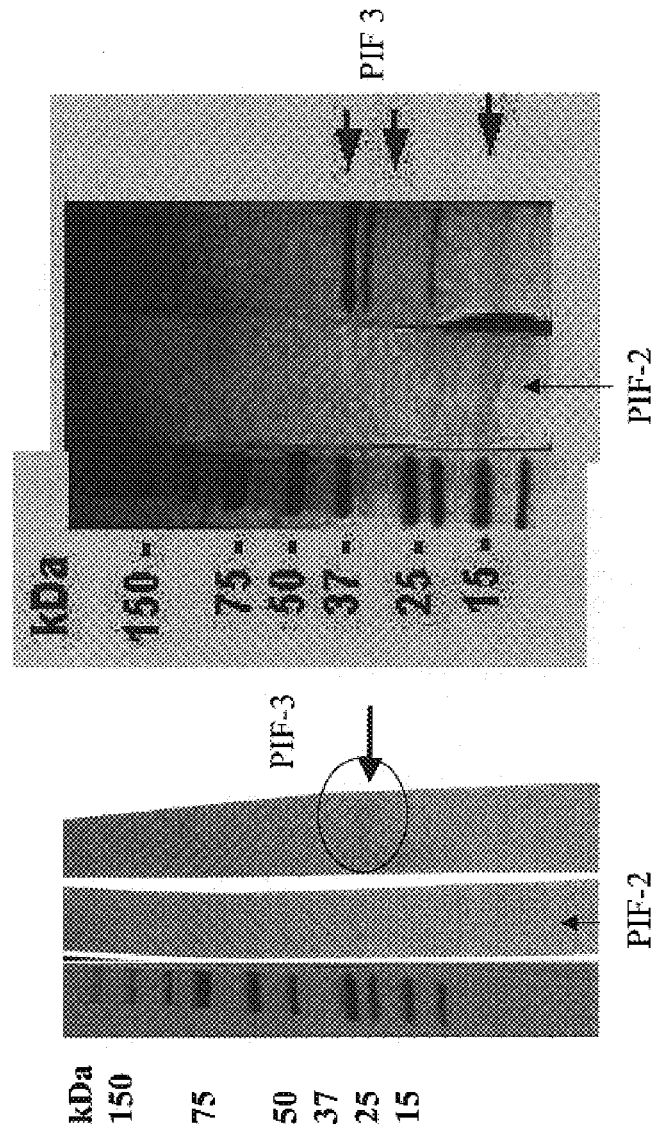

Human placenta was the test antigen. Lanes 1 and 3 were loaded with 50 ug of antigen per lane and lanes 2, 4 and 5 were loaded with 100 ug of antigen per lane. Lanes 1 and 2 were incubated with affi-pure anti-PIF-1 IgY in a 1:50 dilution, goat anti-IgY-HRP in a 1:1000 dilution. Lane 3 was incubated with anti-PIF-1 antibody in 1:200 dilution. Lane 4 was incubated with anti-PIF-2 antibody in 1:50 dilution. Lane 5 was incubated with anti-PIF-3 antibody in 1:50 dilution and goat/anti-rabbit-HRP in a dilution of 1:1000. Results of western blot are shown in FIGS. 7 and 8.

Figure 11:
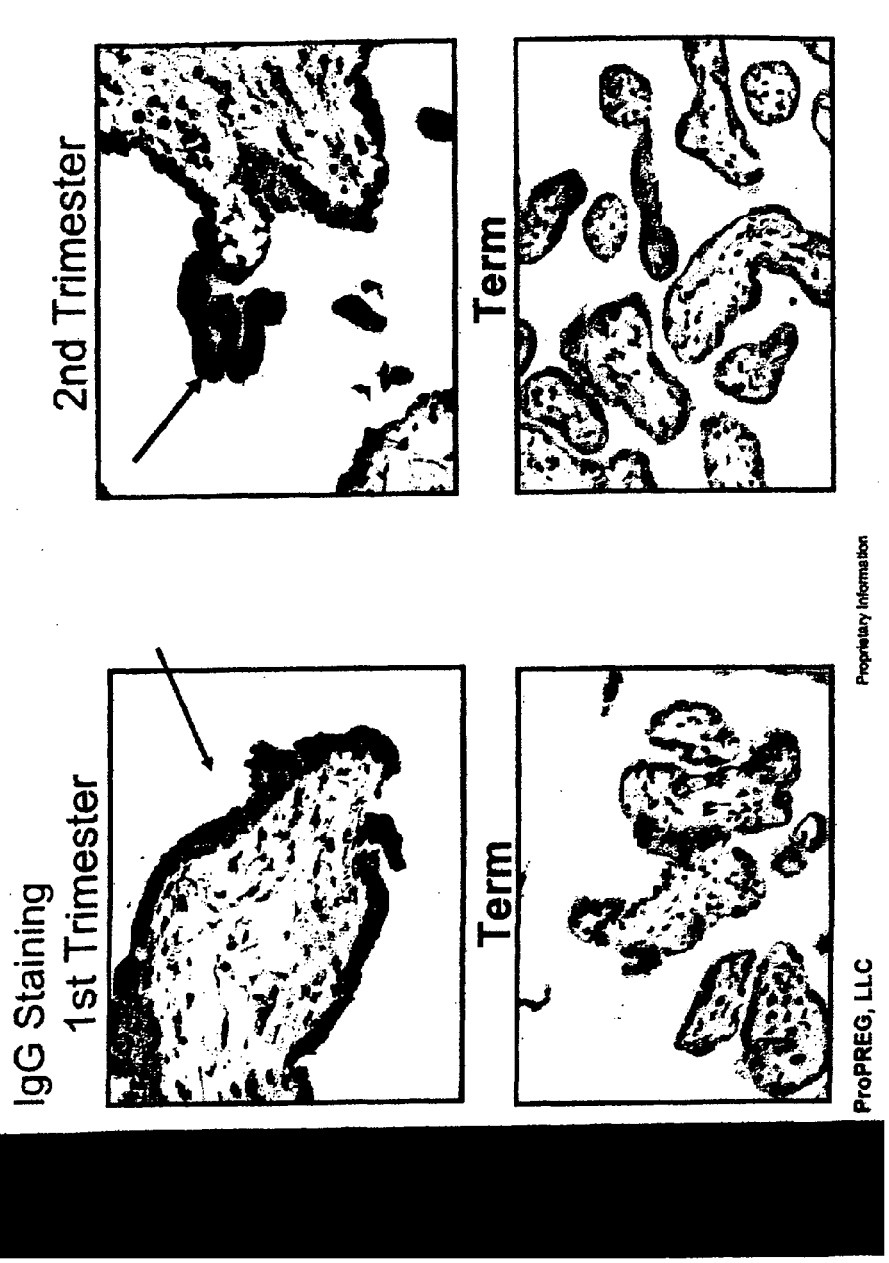
FIG. 11. PIF-1 IgG staining of human placenta during the first trimester, second trimester. PIF-1 appears to be high in the trophoblastic layer while it declined at term.
Figure 12:
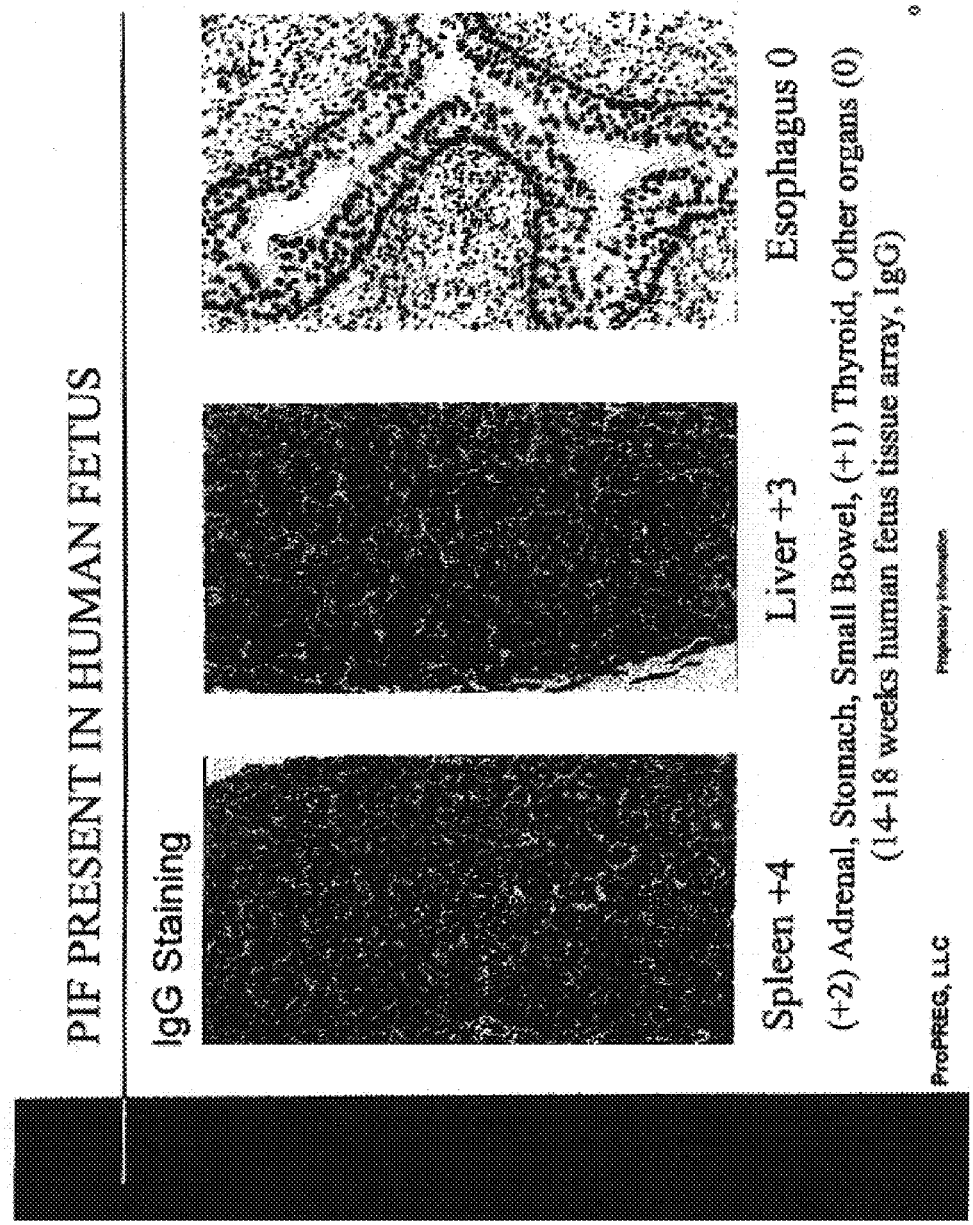
FIG. 12 reflects expression of PIF in various human tissues using IgG in 14-18 weeks human fetus tissue array.

Expression of PIF-1 in human pregnancy tissues was examined using affinity purified IgG using immunohistochemistry methods. Intense trophoblastic expression was found in first and second trimester placenta while expression was low at term as shown in FIG. 11, with respect to the 14-18 weeks fetus using a tissue array (60 samples, covering practically all organs). The highest expression was in the spleen and liver, with lesser in the adrenal, stomach and small bowel with no detectable expression in the esophagus and several other organs as shown in FIG. 12. The presence of PIF was also measured in the adrenal tissue, stomach, small bowel, thyroid and other organs (not shown). Non relevant IgG was used as controls.

Overall this indicates that PIF-1 is expressed in the human placenta and fetus across gestation where it declines at term to facilitate the process of delivery by lowering maternal tolerance for the fetus. With respect for the fetus highest expression appears to be in hemopoietic organs where immune reaction is expected to be the highest.

FIG. 15 shows that in placental sample derived from a patient with premature labor at mid-trimester, PIF expression decreases significantly as examined with the affinity purified PIF-1 IgG antibody. Placental explants were derived from a patient following premature delivery at 26 weeks. Explants were prepared by separating the meaty portion of the placenta rinsed extensively in PBS. Explants were cultured in media with +/− interferon gamma for 24 hours at 37 C with. Tissues were formalin-fixed, paraffin-embedded, cut into 5 μm sections, and placed on Super Plus slides (Fisher Scientific, Pittsburgh, Pa.). Sections were deparaffinized and rehydrated through graded alcohol using standard procedures. Endogenous peroxidase activity was quenched using a 5 min incubation step with 3% $H_2O_2$ in MeOH. Nonspecific binding sites were blocked by incubation with 5% swine serum. Slides were incubated with specific PIF rabbit polyclonal antibody (1:400 dilution, Bio-Synthesis, Inc. Lewisville, Tex.) or appropriate dilution of normal rabbit serum overnight. A Vectastain Elite kit (Vector Laboratories, Burlingame, Calif.) was utilized to visualize antibody binding. PIF-1 staining was basent in the placenta at 0 and 24 hours but was clearly visible if the explants were exposed to INFg. The decline correlated with that of IL10, a major Th2 cytokine. When placental explants are placed in culture and interferon gamma is added, then PIF is reexpressed back to the intensity that was observed in mid trimester. This suggests a reciprocal relationship between cytokines (seen in Table 1) and PIF.

In another example, PIF-1 associated proteins were identified in human placental tissue. Term human placental homogenates were passed through an affinity column of PIF-1 antibody. The mass spectrometry profile following elution by PIF-1 antibody affinity column. Various PIF-1 associated proteins were identified and sequenced following affinity chromatography, including (NM_000039) apolipoprotein A-I precursor [Homo sapiens], electron-transferring-flavoprotein dehydrogenase, (BC017165) similar to triosephosphate isomerase 1 [Homo sapiens], (NM_052925) leukocyte receptor cluster (LRC) member [Homo sapiens], (NM_018141) mitochondrial ribosomal protein S10; mitochondrial 28S ribosomal protein S10 [Homo sapiens], (NM_000518) beta globin [Homo sapiens], (BC012292) heat shock 27 kDa protein 1, stress responsive, estrogen regulated [Homo sapiens] P04792.40, Estradiol beta 1 dehydrogenase 1 P14061.13, Fetal Beta MHC binding factor Q 14297.01, microtubule-associated protein 1A (proliferation-related protein p80 P78559.40). Some of those proteins were not previously described in the placenta. The proteins sequenced appear to show roles in immune function, cytoskeleton, enzyme function, and protein synthesis and cell proliferation. None of the sequenced proteins have sequence homology with PIF-1, therefore it likely reflects, in some cases, that PIF is attached to these proteins reflecting a protein-protein interaction related to the peptides function.

PIF Activity in Human Serum

In a further example, serum samples were obtained at weekly intervals from twenty (20) women in a cross-sectional study (eight (8) in the first trimester, seven (7) in the second trimester, and five (5) in the third trimester) and two (2) women from 5-40 weeks gestation. All women had measurable PIF activity present in serum samples using bioassay (data not shown). No PIF activity was detected in umbilical cord serum using bioassay. Results indicated that PIF is present throughout various stages of pregnancy.

Isolation of PIF Peptides from Pregnant Mammals

Figure 9:
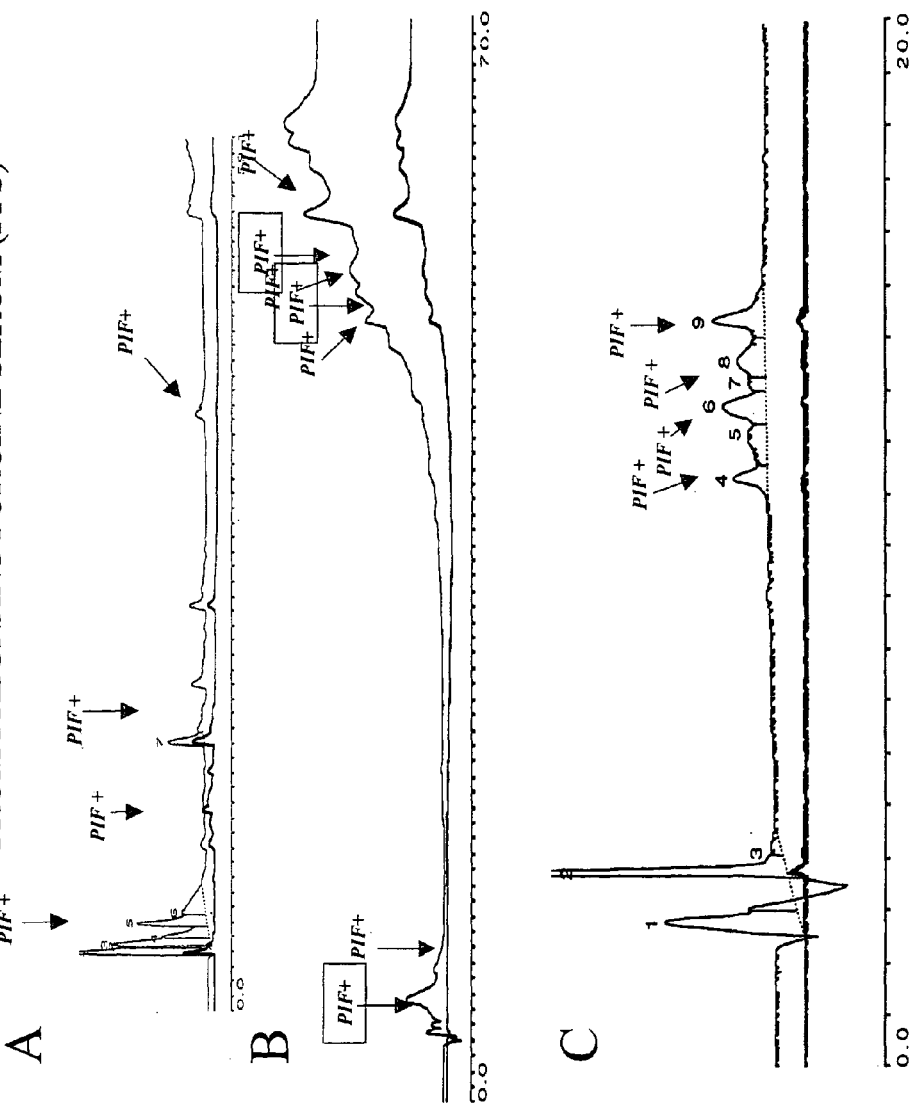
FIG. 9. PIF purification from pregnant porcine serum (PPS). A) HPLC profile of first trimester PPS in a preparative column. B) HPLC profile of PPS-3 kDa previously purified by MabCD2 affinity chromatography. C) HPLC profile of a PIF+peak from PPS-3 kDa previous purified by MabCD2 chromatography affinity and HPLC.
Figure 10:
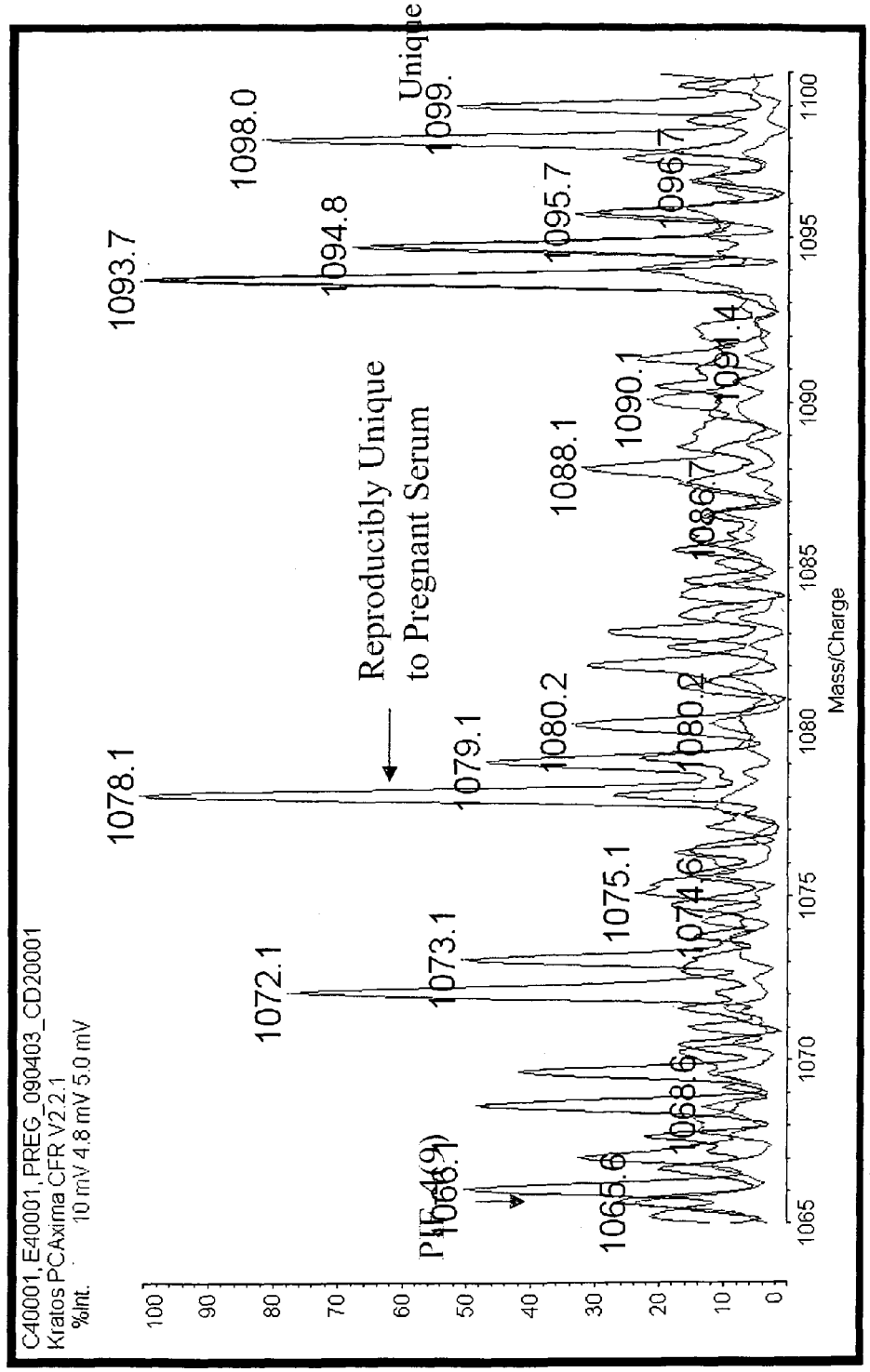
FIG. 10. Mass spectrum based identification of PIF peptides in pregnant pig serum as compared to non-pregnant serum following the use of CD2 based affinity column. Mass of the peptides in the non-pregnant v. pregnant samples revealed significant differences at the 900-1100 molecular weight region, where three distinct peptides were identified.

Blood was collected from known pregnant sow. Serum was separated by centrifugation and the serum was stored at 20 C until use. The collected serum was filtered through a <3 kDa Amicon membrane. The filtrate was further subjected to a CD2 affinity column, as shown in FIG. 9. The collected samples were prepared and mass spectroscopy used to determine the molecular weight of samples by MALDI-TOF workstation. The molecular weight of samples was compared with non-pregnant porcine samples prepared in parallel. A number of peptides unique to pregnancy were isolated molecular weight range of about 1030-1100 daltons as shown in FIG. 10.

In another example, PIF-1 ELISA was used to detect pregnancy in pigs and cows. Using the PIF-1 ELISA competitive Biotin assay, known pregnant and non-pregnant samples were tested. Heat inactivated serum samples were diluted 1/30 and 1/100 and a low dilution difference between pregnant and non-pregnant samples were found for sows and a cow as shown in Tables 8 and 9 below. The estimated PIF-1 in the pregnant sera are 10-30 nM. The heat inactivation helped to reduce the background of the assay generated by some high molecular weight proteins that were recognized by the PIF-1 antibody seen be Western blot (data not shown).

TABLE 8

Detection of PIF in Cow Serum

| Dilution | Pregnancy Status | Neat | Heat Inactivated | % of Neat | Biotin Col. | % of Neat |
|---|---|---|---|---|---|---|
| 1:30 | − | 5.4 | 0.12 | 2 | 5.22 | 97 |
|  | + | 4.2 | 0.22 | 5 | 5.47 | 130 |
| 1:100 | − | 1.51 | — |  | 0.88 | 58 |
|  | + | 2.30 | — |  | 1.48 | 64 |

TABLE 7

Detection of PIF in Sow Serum

| Dilution | Pregnancy Status | Neat | Heat Inactivated | % of Neat | Biotin Col. | % of Neat |
|---|---|---|---|---|---|---|
| 1:30 | − | 30.9 | 3.07 | 10 | 16.6 | 54 |
|  | + | 20.8 | 5.19 | 25 | 12.7 | 61 |

TABLE 7-continued

Detection of PIF in Sow Serum

| Dilution | Pregnancy Status | Neat | Heat Inactivated | % of Neat | Biotin Col. | % of Neat |
|---|---|---|---|---|---|---|
| 1:100 | − | 16.2 | 0.59 | 4 | 6.79 | 42 |
|  | + | 14.7 | 4.58 | 31 | 12.4 | 84 |

In another example, Western blots were prepared from pregnant and non pregnant cow sera (Pelfreeze, Tx) 100 ug of protein were loaded onto a 4-20% gradient SDS-polyacrylamide gel. The separated proteins were electrotransferred to PVDF membrane and, after 1 h blocking [Phosphate-buffer saline Dulbecco's, 1×; 138 mM NaCl, 1.2 mM $KH_2PO_4$, 2.7 mM KCl, 8.1 mM $Na_2HPO_4$ (PBS)+5% dry milk], the membrane was incubated for 1 h at room temperature with a 1/200 dilution of the anti-PIF-1 polyclonal Rabbit IgG in 5% milk-PBS. Following three washes of 5 minutes each in PBS, the membrane was incubated with a 1/1000 dilution of horseradish HRP-conjugated Goat anti-Rabbit IgG (Pierce, N31460, Lot BA623816) for 1 h in 0.5% milk-PBS. Following three washes 5 minutes each in PBS, the final detection was performed using Opti-4CN Substrate Kit (Bio-Rad, Catalog #: 170-8235) according to manufacturer's protocol. Differences in the protein bands were noted between pregnant and non-pregnant sera as shown in FIG. 16.

Figure 17:
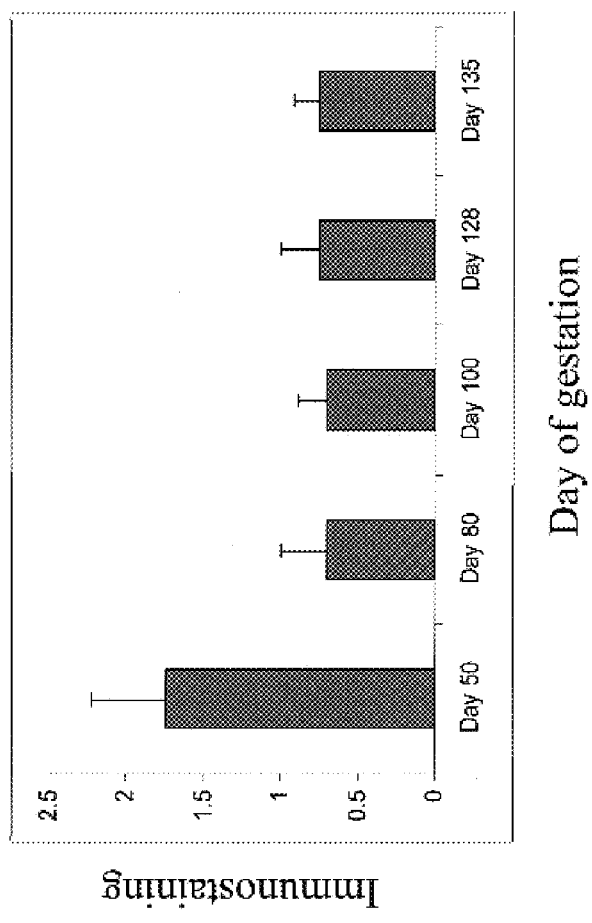
FIG. 17. Gestational age expression of sheep placenta.

In a further example, visual analysis of sheep placenta (R Lea, Aberdeen) was conducted. The collected placenta was embedded in paraffin and slides were prepared. Representative slides exposed to the 1/100 dilution of rabbit affinity purified AbPIF-$1_{(15)}$ antibody. Compared with the non immunized serum, AbPIF-$1_{(15)}$ antibody intensely stained the placenta, as shown in FIG. 17. The DAKO Chemmate system on the autostainer with DAB as the substrate was used. Moreover, the binding was highly specific since no adjacent maternal tissues appeared to be stained by the antibody Samples examined were day 50 (n=4), day 80 (n=7), day 100 (n=7), day 128 (n=4) and day 135 (n=8) Term=145 days (n=9). Based on visual assessment of percent staining, placental levels were highest at day 50 and then declined to day 80 after which they remained constant. This was confirmed by PIF immunostaining at Day 80, showing intesnse staining of the fetal portion of the placenta (data not shown). This pattern reflected the observations that were made with the human placenta.

PIF Presence in Mammalian Blastocysts

Figure 18:
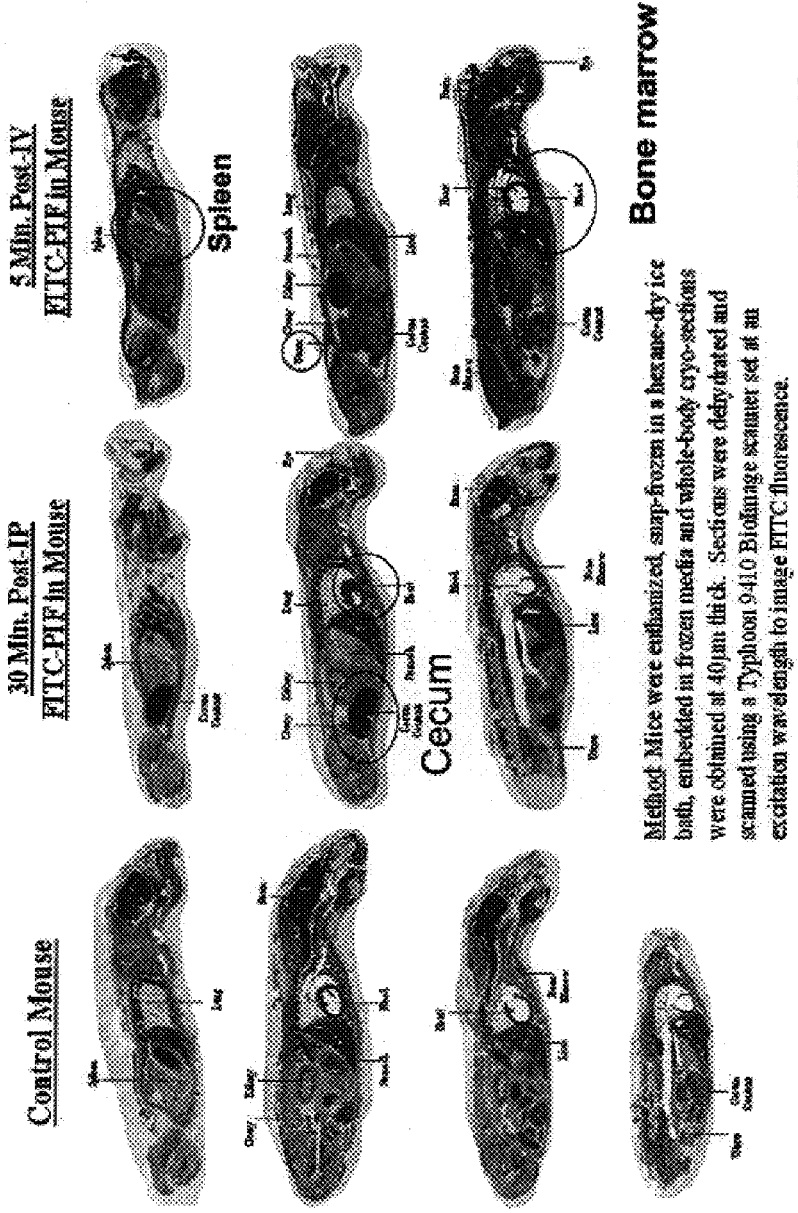
FIG. 18. IgG staining of mouse blastocysts as compared to control using anti-PIF-1 IgG.

Female mice were exposed to males overnight and fertilization was documented by presence of a vaginal plug. Mice were scarified after 3 days and the fallopian tube were flushed out collecting the blastocysts. Blastocysts were placed on slide and were formalin fixed on Super Plus slides (Fisher Scientific, Pittsburgh, Pa.). Endogenous peroxidase activity was quenched using a 5 min incubation step with 3% $H_2O_2$ in MeOH. Nonspecific binding sites were blocked by incubation with 5% swine serum. Slides were incubated with specific PIF rabbit polyclonal antibody (3 ug/ml, Bio-Synthesis, Inc. Lewisville, Tex.) or 3 ug/ml of normal rabbit IgG used as control or preimmune sera. A Vectastain Elite kit (Vector Laboratories, Burlingame, Calif.) was utilized to visualize antibody binding. PIF-1 Ab stained blastocysts were compared to control. As shown in FIG. 18, most staining was located at the polar region of the blastocyst (embryoblast).

PIF Presence in Mammalian Splenocytes and Other Organs

Splenocytes from virgin female C57BL/6 mice were collected and placed in culture with AIMV media overnight in presence of 300 nM PIF-FITC or scrPIF-FITC+/−100 fold respective peptide (Surendra Sharma, Brown U). Cells were evaluated using flow cytometry determining labeled cells population Filled histograms indicate PIF-FITC or scrPIF-FITC alone. As shown in FIG. 13, PIF-1 and scrPIF-1 competitively bind to mouse splenocytes. Empty histograms represent PIF-FITC or scrPIF-FITC staining in the presence of 100-fold excess of corresponding unlabeled peptide. Histograms represent both monocytes and lymphocytes according to scatter gating. The displaced FITC was more complete in the case of PIF-1. However both peptides binding was specific as reflected by presence of receptor on mouse splenocytes. The pattern generated with Ionomycin 50 ng/ml/PMA 500 ng/ml stimulated splenocytes (not shown) was not modified compared to the PIF-1 alone treated cells, indicating independence of calcium channel dependent activity. In contrast, exposure to PHA 1 ug/ml or LPS 2 ug/ml caused a different pattern from controls. However, scr PIF-1 pattern was not modified by exposure to the three experimental conditions. This would indicate that PIF-1 specifically interacts with spleenocytes.

In a further experiment, PIF presence in the spleen was confirmed in vivo, In addition, PIF presence in the cecum, bone marrow and uterus was determined. Adult female rats were injected FITC labeled PIF-1 500 nM in 100 ul volume IV and IP (Eric Solon QPS Inc). 5 and 30 minutes later rats were sacrificed and snap frozen in hexane embedded in frozen media. Whole body 40 um cryo sectioned were obtained and scaaned with a 9140 Typhoon bioimage scanner at a FITC excitation length. As noted in FIG. 19, specific pick was noted in the spleen, bone marrow and uterus of the FITC-PIF. IP pick up was slower with major collection in the cecum.

Genome Analysis

Ten genes isolated from human placenta were analyzed. Seven of the 10 genes were annotated for both human (Hs) and mouse (Mm) genomes. When these were researched on the mpuse microarray dataset for preimplantation development, using either Mm or Hs unigene identifiers returned the same result. The arrays represent four replicated samples averaged from 2AFFY chip platforms. Three of the genes (HSP1, BHSDH, MAPLA) did not change; however, four genes (mRP-S10, ApoA-1, FDH, TPI) were all up-regulated in the blastocyst and there may be a weak tendency for this increase as early as the 8-cell stage.

PIF-1 May Promote Pregnancy and SCR PIF-1 Contraceptive Effects in Mice

Preliminary in vivo assessment of PIF-1 antagonist by using PIF1scr/amide was performed. With the view that PIF-1scr is a peptide, which, in general has a short half-life, estimated to be 30 minutes, a PIF-1scr was generated that had an additional amide group at the C terminus. This was an attempt to make the molecule more stable and have a longer half-life. Following the protocol below: (Dr Hoberman, Argus, Inc) PIF-1scr/amide was introduced two days after estrus to mice through an osmotic mini-pump (Alzet Model 2001; 1 ul/hr for 7 days) containing either 0.9% saline or 150 ug or 800 ug PIF-1scr/amide/day release in saline. The pumps were inserted subcutaneously under ketamine/xylazine anesthesia. Female mice were placed with male mice on the third day afternoon of the expected estrus. Four different groups 5 each were studied, low and high dose PIF-1scr/amide, saline control, and one group with PIF-1. Mating was confirmed by the presence of sperm in the vagina or a copulatory plug the next morning. Pregnancy (or lack thereof) was determined by sacrificing on day 10 after breeding and the uterine horns were examined for implantation sites by using Chicago Blue solution. Results showed a trend towards lower number of implantation sites at the lower PIF-1scr/amide dose v. control group. This however did not reach statistical significance. No differences between high dose PIF-1scr/amide and controls were noted.

PIF-1 has no toxic effects following administration in early pregnancy to pregnant mice. This is evidenced by no significant effect on mouse fetuses number as well there was no effect on maternal body weights were noted among all the tested groups. The group treated with PIF-1 160 ug/kg/day appeared to have increased number of implantation sites and this was associated with a higher rate of fetal survival compared to vehicle treated controls.

Scrambled PIF-1 by Intravaginal Administration
May have a Nontoxic Contraceptive Effect Female mice were mated with mice from the same strain. Subsequently, on day 0 (presumed day of mating) PIF-1scr in saline solution was administered intravaginally twice daily for seven days (Dr Alan Hoberman, Argus, Inc). The dose was 800 ug/day, 150 ug/ml or saline vehicle only (5 animals in each group). Subsequently, mice were sacrificed at day 12 of presumed gestation and Caesarean-sectioned. Corpora lutea, implantation sites and live and dead embryos were recorded. A total of 2 animals in each of the treatment groups and one mouse in the control group failed to conceive. Four out of ten treated animals and only one out of the five control animals conceived, the effect actually being all or none. No toxic or teratogenic effects were noted following the PIF administration since the number of implantation sites and viable embryos were unaffected in those mice that conceived.

Preliminary Study

PIF-1 Antibody and Scrambled PIF-1 Intravenous
Administration is Non Toxic

The contraceptive effect of either 150 ug of PIF-1scr in DMSO or 10 ug-affinity purified PIF-1 (10 animals per group) or 20% DMSO solution (used as controls) was –48-tested using single daily intravenous injections (Dr Alan Hoberman, Argus, Inc). Female mice were placed with male mice on the 3rd day afternoon of the expected estrus. Mating was confirmed by the presence of sperm in the vagina or a copulatory plug the next morning. Subsequently, were injected for 5 days one injection/day. Mice were sacrificed at day 12 of presumed gestation and Caesarean-sectioned. Corpora lutea, implantation sites and number of live and dead embryos were recorded. 2/10 mice in the PIF-1a and PIF-1 antibody group did not get pregnant, while in the control group all mice were pregnant. The effect was all or none since no toxic or teratogenic effects were noted in the mice that conceived.

Although the present invention has been described in considerable detail with reference to certain preferred embodiments thereof, other versions are possible. For example any use of affinity column generated by using PIF-1, PIF-2 and PIF-3 antibodies for the isolation of PIF peptides from biological samples, any peptide derived from pre-implantation embryos that causes enhanced lymphocyte death by any mechanism (apoptosis, etc.), any modified PIF peptides that negate PIF activity and exert biological effects in order to increase immune reaction to enhance immune response in cancer, other immune suppressed conditions, like HIV; and any use of PIF-3 peptide to block HIV infection. A non limiting example is since PIF-3 and PIF-4 share homology with a region of HIV-1 RNA dependent DNA polymerase and the PIF-3 antibody recognizes such a domain on such a major region of HIV-1 virus such compounds could help negate or reduce infectivity of the virus by neutralizing and interdicting its penetration into the cell. The PIF-1 antagonist on the other hand could create a strong $T_H 1$ type immunity thereby overcome immune suppressive conditions that are present for example in cancer.

Although the present invention has been described in considerable detail with reference to certain preferred embodiments thereof, other versions are possible. Therefore the spirit and scope of the appended claims should not be limited to the description and the preferred versions contain within this specification.

REFERENCES

1. S. R. Choudhury, L. A. Knapp, Hum. Reprod. Update 7, 113 (2001).
2. A. K. Abbas, K. M. Murphy, A. Sher, Nature 383, 787 (1996).
3. R. Raghupathy, Immunol. Today 18, 478 (1997).
4. T. G. Wegmann, H. Lin, L. Guilbert, T. R. Mosman, Immunol. Today 14, 353 (1993).
5. E. R. Barnea, K. I. Lahijani, R. Roussev, J. D. Barnea, C. B. Coulam, Am. J. Reprod. Immunol. 32, 133 (1994)
6. R. G. Roussev et al., Mol. Human. Reprod. 2, 883 (1996)
7. R. G. Roussev, E. R. Barnea, E. J. Thomason, C. B. Coulam, Am. J. Reprod. Immunol. 33, 68 (1995).
8. C. B Coulam, R. G. Roussev, E. J. Thomasson, E. R. Barnea, Am. J. Reprod. Immunol. 34, 88 (1995).
9. E. R Barnea et al., Am. J. Reprod. Immunol. 42, 95 (1999).
10. E. R. Barnea, C. B. Coulam, U.S. Pat. No. 5,981,198 (1999).
11. A. C. Cavanagh, H. Morton, Eur. J. Biochem. 222, 551 (1994).
12. E. Critser, J. English, in Immunological Obstetrics, C. B. Coulam, W. P. Faulk, J. A. McIntyre, Eds. (W. W. Norton, New York, 1992), pp. 202-215.
13. S. Heyner, Early Preg. 3, 153 (1997).
14. Circumsporozoite protein-malaria parasite (*Plasmodium falciparum*) (isolate NF54) (Protein accession number S05428)
15. G. Taubes, Science 290, 435 (2000).
16. SMARC32 a putative sperm transmembrane protein related to circumsporozoite protein (Protein accession number AAG31422).
17. D. L. Bodian, E. Y. Jones, K. Harlos, D. I. Stuart, S. J. Davis, Structure 2, 755 (1994).
18. M. P. Piccinni et al., Eur. J. Immunol., 8, 2431 (2001)
19. S. N. Wickramasinghe, S. H. Abdalla, Baillieres Best. Pract. Res. Clin. Haematol. 13, 277 (2000).
20. S. Romagnani, Annu. Rev. Immunol. 12, 227 (1994).
21. G. Chaouat et al., Immunol. 154, 4261 (1995).
22. H. Hong-Nerng et al., Fertil. Steril. 76, 797 (2001).
23. M. Y. Wu et al., Am. J. Reprod. Immunol. 46, 386 (2001).

What is claimed:

1. A synthetic polypeptide consisting of P-G-S-A (SEQ ID NO:19).

2. A composition comprising:
    a synthetic polypeptide consisting of P-G-S-A (SEQ ID NO:19) and an excipient.

3. A composition-comprising:
    a polypeptide consisting of P-G-S-A (SEQ ID NO:19) bonded to a label.

4. The composition of claim 3, wherein said label is selected from the group consisting of FITC, biotin, rhodamine, radioactive isotopes, and fluorescent nanocrystals.

5. A pharmaceutical composition comprising the amino acid sequence a polypeptide consisting of P-G-S-A (SEQ ID NO:19) and a pharmaceutically acceptable excipient.

6. A method of inducing the immune response of a patient comprising:
    administering to said patient an effective amount of a polypeptide consisting of P-G-S-A (SEQ ID NO:19), wherein the amount of TH2 cytokines in said patient is increased.

* * * * *